US009823245B2

(12) United States Patent
Soutter

(10) Patent No.: US 9,823,245 B2
(45) Date of Patent: Nov. 21, 2017

(54) NANODISC CLATHRATES AND USES THEREOF

(71) Applicant: Holly Soutter, Shrewsbury, MA (US)

(72) Inventor: Holly Soutter, Shrewsbury, MA (US)

( * ) Notice: Subject to any disclaimer, the term of this patent is extended or adjusted under 35 U.S.C. 154(b) by 21 days.

(21) Appl. No.: 14/578,412

(22) Filed: Dec. 20, 2014

(65) Prior Publication Data

US 2015/0177234 A1    Jun. 25, 2015

Related U.S. Application Data

(60) Provisional application No. 61/918,686, filed on Dec. 20, 2013.

(51) Int. Cl.
*G01N 33/544* (2006.01)
*G01N 33/543* (2006.01)
*C07K 14/775* (2006.01)
*C07K 14/705* (2006.01)
*C07K 7/23* (2006.01)
*C07K 14/72* (2006.01)

(52) U.S. Cl.
CPC ......... *G01N 33/544* (2013.01); *C07K 14/705* (2013.01); *C07K 14/723* (2013.01); *C07K 14/775* (2013.01); *G01N 33/5432* (2013.01); *G01N 2500/04* (2013.01)

(58) Field of Classification Search
CPC .. G06F 19/16; C27K 14/723; G01N 33/5432; G01N 33/92; C07K 14/775
See application file for complete search history.

(56) References Cited

U.S. PATENT DOCUMENTS

| 7,592,008 | B2 | 9/2009 | Sligar et al. |
| 8,268,357 | B2 | 9/2012 | Ryan et al. |
| 2011/0059549 | A1 | 3/2011 | Coleman et al. |
| 2012/0065104 | A1 | 3/2012 | Wiener et al. |

OTHER PUBLICATIONS

Clathrate definition (last viewed on Nov. 3, 2016).*
Shih et al. Maturation of high-density lipoproteins., J. R. Soc. Interface (2009), vol. 6, pp. 863-871.*
Yoshiura et al., NMR Analyses of the Interaction between CCR5 and Its Ligand Using Functional Reconstitution of CCR5 in Lipid Bilayers., J. Am. Chem. Soc. (2010), vol. 132 (19), pp. 6768-6777.*
P02647 (APOA1_HUMAN) (last viewed on Nov. 4, 2016).*
Hutchings et al., Therapeutic antibodies directed at G protein-coupled receptors., MAbs (2010), vol. 2(6), pp. 594-606.*
Bayburt, T.H. and Sligar, S.G., "Self-assembly of discoidal phospholipid bilayers nanoparticles with membrane scaffold proteins", 2002, Nanoletter, 2:853-856.
Borhani, D.W., et al., "Crystal structure of truncated human apolipoprotein A-I suggests a lipid-bound conformation", 1997, Proc. Natl. Acad. Sci., 94:12291-12296.

(Continued)

*Primary Examiner* — Alexander Kim
(74) *Attorney, Agent, or Firm* — JWIP & Patent Services, LLC; Jacob G. Weintraub, Esq.

(57) ABSTRACT

The present invention describes the novel molecular entities, nanodisc clathrates, the method of preparation, and the use of these molecular entities for solution phase analysis or crystallization.

22 Claims, 12 Drawing Sheets

(56) References Cited

OTHER PUBLICATIONS

Hanson, M.A, et al., "A specific cholesterol binding site is established by the 2.8 angstrom structure of the human beta2-adrenergic receptor", 2008, Structure,16:897-905.

Jaakola, V.P, et al., "The 2.6 angstrom crystal structure of human A2A adenosine receptor bound to antagonist", 2008, Science, 322:1211-1217.

Landau, E.M. and Rosenbusch, J.P., "Lipidic cubic phases: a novel concept for the crystallization of membrane proteins", 1996, Proc. Natl. Acad. Sci., 93:14532-14535.

Nath, A., et al., "Applications of phospholipid bilayer nanodiscs in the study of membrane and membrane proteins", 2007, Biochemistry, 46:2059-2069.

Nollert, P., "Lipidic cubic phases as matrices for membrane protein crystallization", 2004, Methods, 34:348-353.

Siu, F.Y., et al., "Structure of the human glucagon class B G-protein-coupled receptor", 2013, Nature, 499:444-449.

Narne, T., et al., "Structure of beta-1-adrenergic G-protein-coupled receptor", 2008, Nature, 454:486-491.

Denisov, I.G., et al., "Directed self-assembly of monodisperse phospholipid bilayer nanodiscs with controlled size", 2004, J. Am. Chem. Soc., 126:3477-3487.

Fischer, N.O., et al., "Isolation, characterization, and stability of discretely-sized nanolipoprotein particles assembled with apolipophorin-III", 2010, PLOS One, 5:1, e11643.

Hagn, F. et al., "Optimized phospholipid bilayer nanodiscs facilitate high-resolution structure determination of membrane proteins", 2013, J. Am. Chem. Soc., 135:1919-1925.

Habibi, A.E., et al., "Thermostabilization of Bacillus amyloliquefaciens a-amylase by chemical cross-linking", 2006, J. Biotechnology, 123:434-442.

\* cited by examiner

1 = Molecular weight markers
2 = SATA treated nanodisc clatherates
3 = Activated nanodisc clathcrates
4,5 = Rigidified nanodisc clathcrates

SEQUENCE LISTING

```
<160> NUMBER OF SEQ ID NOS: 14

<210> SEQ ID NO 1
<211> LENGTH: 212
<212> TYPE: PRT
<213> ORGANISM: Artificial Sequence
<220> FEATURE:
<223> OTHER INFORMATION: lipid-free scaffold protein

<400> SEQUENCE: 1

Met Gly His His His His His His Ile Glu Gly Ala Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210

<210> SEQ ID NO 2
<211> LENGTH: 234
<212> TYPE: PRT
<213> ORGANISM: Artificial Sequence
<220> FEATURE:
<223> OTHER INFORMATION: lipid-free scaffold protein

<400> SEQUENCE: 2

Met Gly His His His His His His Ile Glu Gly Ala Leu Lys Leu Leu
1               5                   10                  15
```

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
 50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Tyr Leu Asp Asp Phe Gln
                85                  90                  95

Lys Lys Trp Gln Glu Glu Met Glu Leu Tyr Arg Gln Lys Val Glu Pro
            100                 105                 110

Leu Arg Ala Glu Leu Gln Glu Gly Ala Arg Gln Lys Leu His Glu Leu
        115                 120                 125

Gln Glu Lys Leu Ser Pro Leu Gly Glu Glu Met Arg Asp Arg Ala Arg
130                 135                 140

Ala His Val Asp Ala Leu Arg Thr His Leu Ala Pro Tyr Ser Asp Glu
145                 150                 155                 160

Leu Arg Gln Arg Leu Ala Ala Arg Leu Glu Ala Leu Lys Glu Asn Gly
                165                 170                 175

Gly Ala Arg Leu Ala Glu Tyr His Ala Lys Ala Thr Glu His Leu Ser
            180                 185                 190

Thr Leu Ser Glu Lys Ala Lys Pro Ala Leu Glu Asp Leu Arg Gln Gly
        195                 200                 205

Leu Leu Pro Val Leu Glu Ser Phe Lys Val Ser Phe Leu Ser Ala Leu
210                 215                 220

Glu Glu Tyr Thr Lys Lys Leu Asn Thr Gln
225                 230

<210> SEQ ID NO 3
<211> LENGTH: 256
<212> TYPE: PRT
<213> ORGANISM: Artificial Sequence
<220> FEATURE:
<223> OTHER INFORMATION: lipid-free scaffold protein

<400> SEQUENCE: 3

Met Gly His His His His His Ile Glu Gly Ala Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
 50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Tyr Leu Asp Asp Phe Gln Lys Lys Trp Gln Glu Glu Met Glu Leu Tyr
        115                 120                 125

Arg Gln Lys Val Glu Pro Leu Arg Ala Glu Leu Gln Glu Gly Ala Arg
130                 135                 140

Gln Lys Leu His Glu Leu Gln Glu Lys Leu Ser Pro Leu Gly Glu Glu
145                 150                 155                 160

Met Arg Asp Arg Ala Arg Ala His Val Asp Ala Leu Arg Thr His Leu
                165                 170                 175

Ala Pro Tyr Ser Asp Glu Leu Arg Gln Arg Leu Ala Ala Arg Leu Glu
            180                 185                 190

Ala Leu Lys Glu Asn Gly Gly Ala Arg Leu Ala Glu Tyr His Ala Lys
        195                 200                 205

Ala Thr Glu His Leu Ser Thr Leu Ser Glu Lys Ala Lys Pro Ala Leu
    210                 215                 220

Glu Asp Leu Arg Gln Gly Leu Leu Pro Val Leu Glu Ser Phe Lys Val
225                 230                 235                 240

Ser Phe Leu Ser Ala Leu Glu Glu Tyr Thr Lys Lys Leu Asn Thr Gln
                245                 250                 255

<210> SEQ ID NO 4
<211> LENGTH: 278
<212> TYPE: PRT
<213> ORGANISM: Artificial Sequence
<220> FEATURE:
<223> OTHER INFORMATION: lipid-free scaffold protein

<400> SEQUENCE: 4

Met Gly His His His His His His Ile Glu Gly Ala Leu Lys Leu Leu
1               5                   10                  15

Asp Asn Trp Asp Ser Val Thr Ser Thr Phe Ser Lys Leu Arg Glu Gln
                20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
        50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Leu Asp Asp Phe Gln Lys Lys Trp Gln
130                 135                 140

Glu Glu Met Glu Leu Tyr Arg Gln Lys Val Glu Pro Leu Arg Ala Glu
145                 150                 155                 160

Leu Gln Glu Gly Ala Arg Gln Lys Leu His Glu Leu Gln Glu Lys Leu
                165                 170                 175

Ser Pro Leu Gly Glu Glu Met Arg Asp Arg Ala Arg Ala His Val Asp
            180                 185                 190

Ala Leu Arg Thr His Leu Ala Pro Tyr Ser Asp Glu Leu Arg Gln Arg
        195                 200                 205

Leu Ala Ala Arg Leu Glu Ala Leu Lys Glu Asn Gly Gly Ala Arg Leu
    210                 215                 220

Ala Glu Tyr His Ala Lys Ala Thr Glu His Leu Ser Thr Leu Ser Glu
225                 230                 235                 240

Lys Ala Lys Pro Ala Leu Glu Asp Leu Arg Gln Gly Leu Leu Pro Val
                245                 250                 255

```
Leu Glu Ser Phe Lys Val Ser Phe Leu Ser Ala Leu Glu Glu Tyr Thr
            260                 265                 270

Lys Lys Leu Asn Thr Gln
        275
```

<210> SEQ ID NO 5
<211> LENGTH: 223
<212> TYPE: PRT
<213> ORGANISM: Artificial Sequence
<220> FEATURE:
<223> OTHER INFORMATION: lipid-free scaffold protein

<400> SEQUENCE: 5

```
Met Gly His His His His His His Asp Tyr Asp Ile Pro Thr Thr
1               5                   10                  15

Glu Asn Leu Tyr Phe Gln Gly Leu Lys Leu Leu Asp Asn Trp Asp Ser
            20                  25                  30

Val Thr Ser Thr Phe Ser Lys Leu Arg Glu Gln Leu Gly Pro Val Thr
        35                  40                  45

Gln Glu Phe Trp Asp Asn Leu Glu Lys Glu Thr Glu Gly Leu Arg Gln
    50                  55                  60

Glu Met Ser Lys Asp Leu Glu Glu Val Lys Ala Lys Val Gln Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Leu Gly Glu Glu Met
        115                 120                 125

Arg Asp Arg Ala Arg Ala His Val Asp Ala Leu Arg Thr His Leu Ala
    130                 135                 140

Pro Tyr Ser Asp Glu Leu Arg Gln Arg Leu Ala Ala Arg Leu Glu Ala
145                 150                 155                 160

Leu Lys Glu Asn Gly Gly Ala Arg Leu Ala Glu Tyr His Ala Lys Ala
                165                 170                 175

Thr Glu His Leu Ser Thr Leu Ser Glu Lys Ala Lys Pro Ala Leu Glu
            180                 185                 190

Asp Leu Arg Gln Gly Leu Leu Pro Val Leu Glu Ser Phe Lys Val Ser
        195                 200                 205

Phe Leu Ser Ala Leu Glu Glu Tyr Thr Lys Lys Leu Asn Thr Gln
    210                 215                 220
```

<210> SEQ ID NO 6
<211> LENGTH: 200
<212> TYPE: PRT
<213> ORGANISM: Artificial Sequence
<220> FEATURE:
<223> OTHER INFORMATION: lipid-free scaffold protein

<400> SEQUENCE: 6

```
Leu Lys Leu Leu Asp Asn Trp Asp Ser Val Thr Ser Thr Phe Ser Lys
1               5                   10                  15

Leu Arg Glu Gln Leu Gly Pro Val Thr Gln Glu Phe Trp Asp Asn Leu
            20                  25                  30

Glu Lys Glu Thr Glu Gly Leu Arg Gln Glu Met Ser Lys Asp Leu Glu
        35                  40                  45

Glu Val Lys Ala Lys Val Gln Pro Tyr Leu Asp Asp Phe Gln Lys Lys
```

```
            50                  55                  60
Trp Gln Glu Glu Met Glu Leu Tyr Arg Gln Lys Val Glu Pro Leu Arg
 65                  70                  75                  80

Ala Glu Leu Gln Glu Gly Ala Arg Gln Lys Leu His Glu Leu Gln Glu
                 85                  90                  95

Lys Leu Ser Pro Leu Gly Glu Glu Met Arg Asp Arg Ala Arg Ala His
            100                 105                 110

Val Asp Ala Leu Arg Thr His Leu Ala Pro Tyr Ser Asp Glu Leu Arg
            115                 120                 125

Gln Arg Leu Ala Ala Arg Leu Glu Ala Leu Lys Glu Asn Gly Gly Ala
        130                 135                 140

Arg Leu Ala Glu Tyr His Ala Lys Ala Thr Glu His Leu Ser Thr Leu
145                 150                 155                 160

Ser Glu Lys Ala Lys Pro Ala Leu Glu Asp Leu Arg Gln Gly Leu Leu
                165                 170                 175

Pro Val Leu Glu Ser Phe Lys Val Ser Phe Leu Ser Ala Leu Glu Glu
            180                 185                 190

Tyr Thr Lys Lys Leu Asn Thr Gln
        195                 200

<210> SEQ ID NO 7
<211> LENGTH: 212
<212> TYPE: PRT
<213> ORGANISM: Artificial Sequence
<220> FEATURE:
<223> OTHER INFORMATION: lipid-free scaffold protein

<400> SEQUENCE: 7

Met Gly His His His His His His Asp Tyr Asp Ile Pro Thr Thr
 1               5                  10                  15

Glu Asn Leu Tyr Phe Gln Gly Ser Thr Phe Ser Lys Leu Arg Glu Gln
                 20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
 50                  55                  60

Lys Val Gln Pro Tyr Leu Asp Asp Phe Gln Lys Lys Trp Gln Glu Glu
 65                  70                  75                  80

Met Glu Leu Tyr Arg Gln Lys Val Glu Pro Leu Arg Ala Glu Leu Gln
                 85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
```

<210> SEQ ID NO 8
<211> LENGTH: 189
<212> TYPE: PRT
<213> ORGANISM: Artificial Sequence
<220> FEATURE:
<223> OTHER INFORMATION: lipid-free scaffold protein

<400> SEQUENCE: 8

```
Ser Thr Phe Ser Lys Leu Arg Glu Gln Leu Gly Pro Val Thr Gln Glu
1               5                   10                  15

Phe Trp Asp Asn Leu Glu Lys Glu Thr Glu Gly Leu Arg Gln Glu Met
            20                  25                  30

Ser Lys Asp Leu Glu Glu Val Lys Ala Lys Val Gln Pro Tyr Leu Asp
        35                  40                  45

Asp Phe Gln Lys Lys Trp Gln Glu Glu Met Glu Leu Tyr Arg Gln Lys
    50                  55                  60

Val Glu Pro Leu Arg Ala Glu Leu Gln Glu Gly Ala Arg Gln Lys Leu
65                  70                  75                  80

His Glu Leu Gln Glu Lys Leu Ser Pro Leu Gly Glu Glu Met Arg Asp
                85                  90                  95

Arg Ala Arg Ala His Val Asp Ala Leu Arg Thr His Leu Ala Pro Tyr
            100                 105                 110

Ser Asp Glu Leu Arg Gln Arg Leu Ala Ala Arg Leu Glu Ala Leu Lys
        115                 120                 125

Glu Asn Gly Gly Ala Arg Leu Ala Glu Tyr His Ala Lys Ala Thr Glu
    130                 135                 140

His Leu Ser Thr Leu Ser Glu Lys Ala Lys Pro Ala Leu Glu Asp Leu
145                 150                 155                 160

Arg Gln Gly Leu Leu Pro Val Leu Glu Ser Phe Lys Val Ser Phe Leu
                165                 170                 175

Ser Ala Leu Glu Glu Tyr Thr Lys Lys Leu Asn Thr Gln
            180                 185
```

<210> SEQ ID NO 9
<211> LENGTH: 201
<212> TYPE: PRT
<213> ORGANISM: Artificial Sequence
<220> FEATURE:
<223> OTHER INFORMATION: lipid-free scaffold protein

<400> SEQUENCE: 9

```
Met Gly His His His His His His Asp Tyr Asp Ile Pro Thr Thr
1               5                   10                  15

Glu Asn Leu Tyr Phe Gln Gly Pro Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110
```

```
His Val Asp Ala Leu Arg Thr His Leu Ala Pro Tyr Ser Asp Glu Leu
            115                 120                 125

Arg Gln Arg Leu Ala Ala Arg Leu Glu Ala Leu Lys Glu Asn Gly Gly
        130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 10
<211> LENGTH: 201
<212> TYPE: PRT
<213> ORGANISM: Artificial Sequence
<220> FEATURE:
<223> OTHER INFORMATION: lipid-free scaffold protein

<400> SEQUENCE: 10

Met Gly His His His His His His Asp Tyr Asp Ile Pro Thr Thr
1               5                   10                  15

Glu Asn Leu Tyr Phe Gln Gly Ser Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
50                  55                  60

Lys Trp Gln Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 11
<211> LENGTH: 177
<212> TYPE: PRT
<213> ORGANISM: Artificial Sequence
<220> FEATURE:
<223> OTHER INFORMATION: lipid-free scaffold protein

<400> SEQUENCE: 11

Ser Val Thr Gln Glu Phe Trp Asp Asn Leu Glu Lys Glu Thr Glu Gly
1               5                   10                  15
```

Leu Arg Gln Met Ser Lys Asp Leu Glu Glu Val Lys Ala Lys Val Gln
           20                  25                  30

Pro Tyr Leu Asp Asp Phe Gln Lys Lys Trp Gln Glu Glu Met Glu Leu
                35                  40                  45

Tyr Arg Gln Lys Val Glu Pro Leu Arg Ala Glu Leu Gln Glu Gly Ala
 50                  55                  60

Arg Gln Lys Leu His Glu Leu Gln Glu Lys Leu Ser Pro Leu Gly Glu
 65                  70                  75                  80

Glu Met Arg Asp Arg Ala Arg Ala His Val Asp Ala Leu Arg Thr His
                 85                  90                  95

Leu Ala Pro Tyr Ser Asp Glu Leu Arg Gln Arg Leu Ala Ala Arg Leu
                100                 105                 110

Glu Ala Leu Lys Glu Asn Gly Gly Ala Arg Leu Ala Glu Tyr His Ala
                115                 120                 125

Lys Ala Thr Glu His Leu Ser Thr Leu Ser Glu Lys Ala Lys Pro Ala
130                 135                 140

Leu Glu Asp Leu Arg Gln Gly Leu Leu Pro Val Leu Glu Ser Phe Lys
145                 150                 155                 160

Val Ser Phe Leu Ser Ala Leu Glu Glu Tyr Thr Lys Lys Leu Asn Thr
                165                 170                 175

Gln

<210> SEQ ID NO 12
<211> LENGTH: 245
<212> TYPE: PRT
<213> ORGANISM: Artificial Sequence
<220> FEATURE:
<223> OTHER INFORMATION: lipid-free scaffold protein

<400> SEQUENCE: 12

Met Gly His His His His His His Asp Tyr Asp Ile Pro Thr Thr
 1               5                  10                  15

Glu Asn Leu Tyr Phe Gln Gly Leu Lys Leu Leu Asp Asn Trp Asp Ser
                 20                  25                  30

Val Thr Ser Thr Phe Ser Lys Leu Arg Glu Gln Leu Gly Pro Val Thr
                 35                  40                  45

Gln Glu Phe Trp Asp Asn Leu Glu Lys Glu Thr Glu Gly Leu Arg Gln
 50                  55                  60

Glu Met Ser Lys Asp Leu Glu Glu Val Lys Ala Lys Val Gln Pro Tyr
 65                  70                  75                  80

Leu Asp Asp Phe Gln Lys Lys Trp Gln Glu Glu Met Glu Leu Tyr Arg
                 85                  90                  95

Gln Lys Val Glu Pro Leu Arg Ala Glu Leu Gln Glu Gly Ala Arg Gln
                100                 105                 110

Glu Met Glu Leu Tyr Arg Gln Lys Val Glu Pro Leu Arg Ala Glu Leu
                115                 120                 125

Gln Glu Gly Ala Arg Gln Lys Leu His Glu Leu Gln Glu Lys Leu Ser
            130                 135                 140

Pro Leu Gly Glu Glu Met Arg Asp Arg Ala Arg Ala His Val Asp Ala
145                 150                 155                 160

Leu Arg Thr His Leu Ala Pro Tyr Ser Asp Glu Leu Arg Gln Arg Leu
                165                 170                 175

Ala Ala Arg Leu Glu Ala Leu Lys Glu Asn Gly Gly Ala Arg Leu Ala
                180                 185                 190

```
Glu Tyr His Ala Lys Ala Thr Glu His Leu Ser Thr Leu Ser Glu Lys
            195                 200                 205

Ala Lys Pro Ala Leu Glu Asp Leu Arg Gln Gly Leu Leu Pro Val Leu
210                 215                 220

Glu Ser Phe Lys Val Ser Phe Leu Ser Ala Leu Glu Glu Tyr Thr Lys
225                 230                 235                 240

Lys Leu Asn Thr Gln
            245

<210> SEQ ID NO 13
<211> LENGTH: 267
<212> TYPE: PRT
<213> ORGANISM: Artificial Sequence
<220> FEATURE:
<223> OTHER INFORMATION: lipid-free scaffold protein

<400> SEQUENCE: 13

Met Gly His His His His His His Asp Tyr Asp Ile Pro Thr Thr
1               5                   10                  15

Glu Asn Leu Tyr Phe Gln Gly Leu Lys Leu Leu Asp Asn Trp Asp Ser
            20                  25                  30

Val Thr Ser Thr Phe Ser Lys Leu Arg Glu Gln Leu Gly Pro Val Thr
        35                  40                  45

Gln Glu Phe Trp Asp Asn Leu Glu Lys Glu Thr Glu Gly Leu Arg Gln
    50                  55                  60

Glu Met Ser Lys Asp Leu Glu Glu Val Lys Ala Lys Val Gln Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 14
<211> LENGTH: 289
<212> TYPE: PRT
<213> ORGANISM: Artificial Sequence
<220> FEATURE:
```

```
<223> OTHER INFORMATION: lipid-free scaffold protein

<400> SEQUENCE: 14

Met Gly His His His His His His Asp Tyr Asp Ile Pro Thr Thr
1               5                   10                  15

Glu Asn Leu Tyr Phe Gln Gly Leu Lys Leu Leu Asp Asn Trp Asp Ser
            20                  25                  30

Val Thr Ser Thr Phe Ser Lys Leu Arg Glu Gln Leu Gly Pro Val Thr
        35                  40                  45

Gln Glu Phe Trp Asp Asn Leu Glu Lys Glu Thr Glu Gly Leu Arg Gln
    50                  55                  60

Glu Met Ser Lys Asp Leu Glu Glu Val Lys Ala Lys Val Gln Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Leu Gly Glu Glu Met
        115                 120                 125

Arg Asp Arg Ala Arg Ala His Val Asp Ala Leu Arg Thr His Leu Ala
    130                 135                 140

Pro Tyr Leu Asp Asp Phe Gln Lys Lys Trp Gln Glu Glu Met Glu Leu
145                 150                 155                 160

Tyr Arg Gln Lys Val Glu Pro Leu Arg Ala Glu Leu Gln Glu Gly Ala
                165                 170                 175

Arg Gln Lys Leu His Glu Leu Gln Glu Lys Leu Ser Pro Leu Gly Glu
            180                 185                 190

Glu Met Arg Asp Arg Ala Arg Ala His Val Asp Ala Leu Arg Thr His
        195                 200                 205

Leu Ala Pro Tyr Ser Asp Glu Leu Arg Gln Arg Leu Ala Ala Arg Leu
    210                 215                 220

Glu Ala Leu Lys Glu Asn Gly Gly Ala Arg Leu Ala Glu Tyr His Ala
225                 230                 235                 240

Lys Ala Thr Glu His Leu Ser Thr Leu Ser Glu Lys Ala Lys Pro Ala
                245                 250                 255

Leu Glu Asp Leu Arg Gln Gly Leu Leu Pro Val Leu Glu Ser Phe Lys
            260                 265                 270

Val Ser Phe Leu Ser Ala Leu Glu Glu Tyr Thr Lys Lys Leu Asn Thr
        275                 280                 285

Gln
```

NANODISC CLATHRATES AND USES THEREOF

In accordance with 37 C.F.R. §1.821-1.824, a Sequence Listing accompanies this application. The Sequence Listing is incorporated herein by reference in its entirety and is to be entered into the application in its entirety.

BACKGROUND OF THE INVENTION

Many of the targets of drug discovery efforts are proteins, including membrane proteins. To date, the ability to accumulate relevant structural and functional information for membrane proteins through the generation of ligand-protein complex structures has been limited. And the inability to generate these structures is in part due to the limitations that arise because of the requirement for the use of detergents to extract, purify and crystallize membrane proteins.

To this end, there has been recent progress in generating crystal structures of seven-transmembrane, G-protein coupled receptors (GPCR's) such as β1 and β2-adrenergic receptors (Warne, et al., 2008; Hanson, et al., 2008)) the adenosine A(2A) receptor (Jaakola, et al., 2008) and the glucagon receptor, GCGR (siu, et al., 2013). However, these structures were generated using highly mutated forms of the proteins, including multiple point mutations and the insertion of a large fusion domains; and these mutations often alter the ligand binding characteristics of these proteins. Additionally, the crystals used to generate these GPCR structures were grown using the technique of lipidic-cubic phase crystallization which is limited in its utility due to the difficulties in handling the lipid-protein mixture, visualizing crystals within the lipid matrix and retrieving the small crystals from the lipid matrix (Landau & Rosenbusch 1996; Nollert 2004).

Clearly, there is a need for additional techniques or methods to gain increased structural understanding of wild-type membrane proteins. Ideally, one would like to identify a robust crystallization technique that would allow for the crystallization of fully functional, wild-type membrane proteins without the presence of detergents, e.g., using vapor-diffusion crystallization.

SUMMARY OF THE INVENTION

As such, the present invention provides nanodisc clathrates, methods of preparation, and the use of these novel molecular entities for solution phase analysis or crystallization. In particular, the present invention provides methods of preparation of the nanodisc clathrates of the invention utilizing a nanodisc clathrate scaffold containing moieties suitable for cross-linking to form rigidified nanodisc clathrates.

Successful crystallization and structure solution of a membrane protein-nanodisc assembly using the methods provided herein allows for the implementation of a structure solution platform that does not require mutation of the membrane protein of interest or use of detergents in the crystallization. Moreover, the structures obtained using this method represent biologically relevant conformations of the proteins and allow for a greater understanding of their structure-function relationships. The determination of protein-ligand complexes using this method enables biologically relevant structure based drug design efforts allowing for the development of more potent, selective drugs which target membrane proteins.

Accordingly, in one aspect, the invention provides a nanodisc clathrate comprising a protein integrated into a rigidified nanodisc clathrate scaffold.

In another embodiment, the invention provides a method of preparation of a nanodisc clathrate scaffold comprising the steps of
  (a) pre-selecting a lipid-free scaffold protein to contain moieties suitable for cross-linking, and in sufficient number to achieve rigidification upon the addition of a cross-linking agent; and
  (b) combining the lipid-free scaffold protein and a lipid in an environment of reduced detergent, forming a nanodisc clathrate scaffold.

In another aspect, the invention provides a method of preparation of a nanodisc clathrate comprising the steps of
  (a) pre-selecting a lipid-free scaffold protein to contain moieties suitable for cross-linking, and in sufficient number to achieve rigidification upon the addition of a cross-linking agent; and
  (b) combining the lipid-free scaffold protein, a lipid, and a protein to be integrated within a nanodisc clathrate scaffold in an environment of reduced detergent, forming a nanodisc clathrate.

In another embodiment, the invention provides a method of preparation of a nanodisc clathrate scaffold comprising the steps of
  (a) pre-selecting a lipid-free scaffold protein to contain moieties suitable for cross-linking, and in sufficient number to achieve rigidification upon the addition of a cross-linking agent;
  (b) modification of said moieties of the pre-selected, lipid-free scaffold protein to contain chemically reactive groups suitable for controlled activation upon the addition of an activating reagent; and
  (c) combining the modified lipid-free scaffold protein and a lipid in an environment of reduced detergent, forming a nanodisc clathrate scaffold.

In another aspect, the invention provides a method of preparation of a nanodisc clathrate comprising the steps of
  (a) pre-selecting a lipid-free scaffold protein to contain moieties suitable for cross-linking, and in sufficient number to achieve rigidification upon the addition of a cross-linking agent;
  (b) modification of said moieties of the pre-selected, lipid-free scaffold protein to contain chemically reactive groups suitable for controlled activation upon the addition of an activating reagent; and
  (c) combining the modified lipid-free scaffold protein, a lipid, and a protein to be integrated within a nanodisc clathrate scaffold in an environment of reduced detergent, forming a nanodisc clathrate.

In another aspect, the present invention provides a method of producing X-ray quality crystals of a protein comprising the step of subjecting a nanodisc clathrate of claim 1 to crystallization screening, such that an X-ray quality crystal is produced.

In yet another aspect, the present invention provides a method of solution phase analysis of potential drug candidates comprising the steps of
  (a) pre-selecting a target protein for screening potential drug candidates;
  (b) preparing a nanodisc clathrate comprising a protein integrated into a rigidified nanodisc clathrate scaffold, wherein the integrated protein is said target protein; and
  (c) combining said nanodisc clathrate with one or more potential drug candidates in solution; and (d) analyzing the results of said combination, providing a solution phase analysis of the potential drug candidates

DETAILED DESCRIPTION OF THE INVENTION

The present invention provides nanodisc clathrates that allow investigation into protein structure, e.g., membrane protein structure, without the need for detergents, and which are soluble in aqueous buffer. In this way, they are more suitable for in vitro assays, high-throughput screening, solution phase structural analysis using nuclear magnetic resonance imaging (NMR), Surface Plasmon Resonance analysis (SPR) or other analyses that may be negatively affected by the presence of detergents. Moreover, the membrane protein inside the nanodisc clathrate is in a more native-like environment, a lipid bilayer, and the lipid composition of the nanodisc clathrate may be varied to more closely mimic the native bilayer of the membrane protein.

Furthermore, the present invention, including novel molecular entities, methods of preparation, and uses thereof will be described with reference to the following definitions that, for convenience, are set forth below. Unless otherwise specified, the below terms used herein are defined as follows:

I. Definitions

The term "cross-linking" is art-recognized, and used herein to describe the chemical bond formation that occurs in a controlled manner upon addition of a cross-linking agent, e.g., subsequent to an activating reagent.

Figure 1:
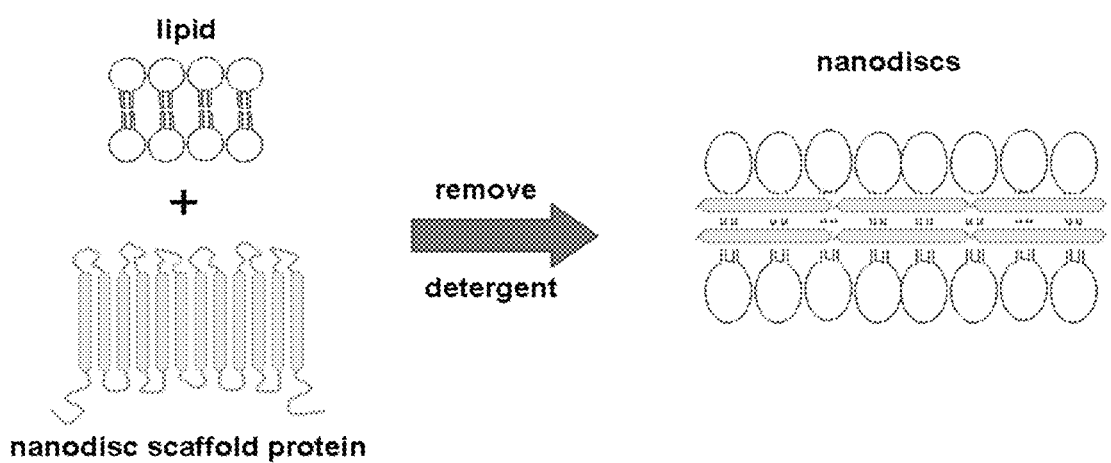
FIG. 1 is a graphical depiction of the formation of nanodiscs from lipid and nanodisc scaffold protein.

The term "nanodisc" is well known in the art, and is distinct from the nanodisc clathrates described herein. Nanodiscs are discoidal lipid bilayers encompassed by a protein scaffold. Certain exemplary protein scaffolds are derived from the carboxy-terminal tail of apolipoprotein A-I and is an amphipathic, alpha-helical protein punctuated by prolines (Bayburt, et al., 2004). Mixture of the lipid-free scaffold protein with lipids results in a self-assembled nanoparticle containing a lipid bilayer roughly 10 nm in diameter with two copies of the scaffold protein wrapped around the perimeter of the disc in an anti-parallel fashion. The hydrophobic face of the scaffold protein serves to sequester the hydrocarbon tails of the phospholipids away from solvent (Borhani, et al., 1997). The resulting particle is aqueously soluble and stable. (See also FIG. 1)

The language, "nanodisc clathrate scaffold" as used herein, describes an assembled nanodisc capable of integrating a protein, e.g., a membrane protein, prepared from a lipid and a lipid-free nanodisc scaffold protein that is constructed with two or more moieties suitable for cross-linking. These moieties are generated by the modification of specific regions of the pre-selected, lipid-free scaffold protein to contain chemically reactive groups ideal for cross-linking upon the addition of an activating reagent and subsequent cross-linking agent to form a rigidified nanodisc clathrate scaffold.

The term "lipid" as used herein, describes any of various substances that are soluble in nonpolar organic solvents, that are usually insoluble in water, that with proteins and carbohydrates constitute the principal structural components of living cells, and that include fats, waxes, phosphatides, cerebrosides, sphingolipids and related and derived compounds. Exemplary phospholipids include those from natural sources, synthetic sources, saturated, unsaturated, mixed acyl, diether and lyso, for example, phosphatidylcholine, phosphatidic acid, phosphatidylethanolamine, phosphatidylglycerol, phosphatidylserine, phosphatidylinositol, phosphatidylinositolphosphate, or cardiolipin. In a particular embodiment, the phospholipid is 1-palmitoyl-2-oleoyl-sn-glycero-3-phosphocholine or 1,2-dimyristoyl-sn-glycero-3-phosphocholine. Exemplary sphingolipids include those from natural sources, synthetic sources, phosphorylated, unphosphorylated, methylated), for example, sphingosines, ceramides, sphingomyelin, gangliosides, glycosphingolipids, phosphosphingolipids, or phytosphingosine. In a particular embodiment the sphingolipid is sphingosine or ceramide. Exemplary sterols include those from natural sources, synthetic sources, substituted oxysterols and derivatives, for example, cholesterol or trihydroxycholestanoic acid. In certain embodiments, the lipid is Coenzyme A: free acid, acylated, saturated or unsaturated. Neutral lipids include, for example, diacylglycerol, glycosylated diacylglycerols, prostaglandins, prenols, N-acyl glycine, and very long chain fatty acids. In a particular embodiment, the lipid is diacylglycerol or PGF1α.

The language "lipid free scaffold protein" describes the lipid-free form of the nanodisc scaffold protein. The lipid free scaffold protein is a 100 to 200 amino acid protein that is an amphipathic alpha-helical protein delineated by one or more proline residues. In certain embodiments, the lipid free scaffold protein may be selected from the following list of amino acid sequences described in Denisov, et al., 2004:

(a) MSP1 Sequence (SEQ ID NO: 1):
MGHHHHHHIEGALKLLDNWDSVTSTFSKLREQLGPVTQEFWDNLEKETEG

LRQEMSKDLEEVKAKVQPYLDDFQKKWQEEMELYRQKVEPLRAELQEGAR

QKLHELQEKLSPLGEEMRDRARAHVDALRTHLAPYSDELRQRLAARLEAL

KENGGARLAEYHAKATEHLSTLSEKAKPALEDLRQGLLPVLESFKVSFLS

ALEEYTKKLNTQ (b) MSP1E1 Sequence (SEQ ID NO: 2):
MGHHHHHHIEGALKLLDNWDSVTSTFSKLREQLGPVTQEFWDNLEKETEG

LRQEMSKDLEEVKAKVQPYLDDFQKKWQEEMELYRQKVEPYLDDFQKKWQ

EEMELYRQKVEPLRAELQEGARQKLHELQEKLSPLGEEMRDRARAHVDAL

RTHLAPYSDELRQRLAARLEALKENGGARLAEYHAKATEHLSTLSEKAKP

ALEDLRQGLLPVLESFKVSFLSALEEYTKKLNTQ (c) MSP1E2 Sequence (SEQ ID NO: 3):
MGHHHHHHIEGALKLLDNWDSVTSTFSKLREQLGPVTQEFWDNLEKETEG

LRQEMSKDLEEVKAKVQPYLDDFQKKWQEEMELYRQKVEPLRAELQEGAR

QKLHELQEKLSPYLDDFQKKWQEEMELYRQKVEPLRAELQEGARQKLHEL

QEKLSPLGEEMRDRARAHVDALRTHLAPYSDELRQRLAARLEALKENGGA

RLAEYHAKATEHLSTLSEKAKPALEDLRQGLLPVLESFKVSFLSALEEYT

KKLNTQ (d) MSP1E3 Sequence (SEQ ID NO: 4):
MGHHHHHHIEGALKLLDNWDSVTSTFSKLREQLGPVTQEFWDNLEKETEG

LRQEMSKDLEEVKAKVQPYLDDFQKKWQEEMELYRQKVEPLRAELQEGAR

QKLHELQEKLSPLGEEMRDRARAHVDALRTHLAPYLDDFQKKWQEEMELY

RQKVEPLRAELQEGARQKLHELQEKLSPLGEEMRDRARAHVDALRTHLAP

YSDELRQRLAARLEALKENGGARLAEYHAKATEHLSTLSEKAKPALEDLR

QGLLPVLESFKVSFLSALEEYTKKLNTQ (e) MSP1TEV Sequence (SEQ ID NO: 5):
MGHHHHHHDYDIPTTENLYFQGLKLLDNWDSVTSTFSKLREQLGPVTQE

FWDNLEKETEGLRQEMSKDLEEVKAKVQPYLDDFQKKWQEEMELYRQKVE

PLRAELQEGARQKLHELQEKLSPLGEEMRDRARAHVDALRTHLAPYSDEL

RQRLAARLEALKENGGARLAEYHAKATEHLSTLSEKAKPALEDLRQGLLP

VLESFKVSFLSALEEYTKKLNTQ (f) MSP1(-)Sequence (SEQ ID NO: 6):
LKLLDNWDSVTSTFSKLREQLGPVTQEFWDNLEKETEGLRQEMSKDLEEV

KAKVQPYLDDFQKKWQEEMELYRQKVEPLRAELQEGARQKLHELQEKLSP

LGEEMRDRARAHVDALRTHLAPYSDELRQRLAARLEALKENGGARLAEYH

AKATEHLSTLSEKAKPALEDLRQGLLPVLESFKVSFLSALEEYTKKLNTQ (g) MSP1D1 Sequence (SEQ ID NO: 7):
MGHHHHHHDYDIPTTENLYFQGSTFSKLREQLGPVTQEFWDNLEKETEG

LRQEMSKDLEEVKAKVQPYLDDFQKKWQEEMELYRQKVEPLRAELQEGAR

QKLHELQEKLSPLGEEMRDRARAHVDALRTHLAPYSDELRQRLAARLEAL

KENGGARLAEYHAKATEHLSTLSEKAKPALEDLRQGLLPVLESFKVSFLS

ALEEYTKKLNTQ (h) MSP1D1(-)Sequence (SEQ ID NO: 8):
STFSKLREQLGPVTQEFWDNLEKETEGLRQEMSKDLEEVKAKVQPYLDDF

QKKWQEEMELYRQKVEPLRAELQEGARQKLHELQEKLSPLGEEMRDRARA

HVDALRTHLAPYSDELRQRLAARLEALKENGGARLAEYHAKATEHLSTLS

EKAKPALEDLRQGLLPVLESFKVSFLSALEEYTKKLNTQ

-continued (i) MSP1D2 Sequence (SEQ ID NO: 9):
MGHHHHHHHDYDIPTTENLYFQGPVTQEFWDNLEKETEGLRQEMSKDLEE

VKAKVQPYLDDFQKKWQEEMELYRQKVEPLRAELQEGARQKLHELQEKLS

PLGEEMRDRARAHVDALRTHLAPYSDELRQRLAARLEALKENGGARLAEY

HAKATEHLSTLSEKAKPALEDLRQGLLPVLESFKVSFLSALEEYTKKLNT

Q (j) MSP1D2P23S Sequence (SEQ ID NO: 10):
MGHHHHHHHDYDIPTTENLYFQGSVTQEFWDNLEKETEGLRQEMSKDLEE

VKAKVQPYLDDFQKKWQEEMELYRQKVEPLRAELQEGARQKLHELQEKLS

PLGEEMRDRARAHVDALRTHLAPYSDELRQRLAARLEALKENGGARLAEY

HAKATEHLSTLSEKAKPALEDLRQGLLPVLESFKVSFLSALEEYTKKLNT

Q (k) MSP1D2P23S(-)Sequence (SEQ ID NO: 11):
SVTQEFWDNLEKETEGLRQMSKDLEEVKAKVQPYLDDFQKKWQEEMELYR

QKVEPLRAELQEGARQKLHELQEKLSPLGEEMRDRARAHVDALRTHLAPY

SDELRQRLAARLEALKENGGARLAEYHAKATEHLSTLSEKAKPALEDLRQ

GLLPVLESFKVSFLSALEEYTKKLNTQ (l) MSP1E1TEV Sequence (SEQ ID NO: 12):
MGHHHHHHHDYDIPTTENLYFQGLKLLDNWDSVTSTFSKLREQLGPVTQE

FWDNLEKETEGLRQEMSKDLEEVKAKVQPYLDDFQKKWQEEMELYRQKVE

PYLDDFQKKWQEEMELYRQKVEPLRAELQEGARQKLHELQEKLSPLGEEM

RDRARAHVDALRTHLAPYSDELRQRLAARLEALKENGGARLAEYHAKATE

HLSTLSEKAKPALEDLRQGLLPVLESFKVSFLSALEEYTKKLNTQ (m) MSP1E2TEV Sequence (SEQ ID NO: 13):
MGHHHHHHHDYDIPTTENLYFQGLKLLDNWDSVTSTFSKLREQLGPVTQE

FWDNLEKETEGLRQEMSKDLEEVKAKVQPYLDDFQKKWQEEMELYRQKVE

PLRAELQEGARQKLHELQEKLSPYLDDFQKKWQEEMELYRQKVEPLRAEL

QEGARQKLHELQEKLSPLGEEMRDRARAHVDALRTHLAPYSDELRQRLAA

RLEALKENGGARLAEYHAKATEHLSTLSEKAKPALEDLRQGLLPVLESFK

VSFLSALEEYTKKLNTQ (n) MSP1E3TEV Sequence (SEQ ID NO: 13):
MGHHHHHHHDYDIPTTENLYFQGLKLLDNWDSVTSTFSKLREQLGPVTQE

FWDNLEKETEGLRQEMSKDLEEVKAKVQPYLDDFQKKWQEEMELYRQKVE

PLRAELQEGARQKLHELQEKLSPLGEEMRDRARAHVDALRTHLAPYLDDF

QKKWQEEMELYRQKVEPLRAELQEGARQKLHELQEKLSPLGEEMRDRARA

HVDALRTHLAPYSDELRQRLAARLEALKENGGARLAEYHAKATEHLSTLS

EKAKPALEDLRQGLLPVLESFKVSFLSALEEYTKKLNTQ

As used herein, the term "rigidified" describes the nanodisc clathrate scaffolds provided herein, which possess moieties suitable for cross-linking, and which have been cross-linked. The process of cross-linking these moieties is referred to herein as "rigidification."

As used herein, the term "integrated" describes the presence of a protein encapsulated within a nanodisc clathrate scaffold. The proteins integrated into the rigidified nanodisc clathrates of the present invention allow for superior characterization and utility in structure determination or solution phase analysis, than simple nanodiscs known in the art.

The term "protein," as used herein describes insoluble proteins, i.e., any of a large class of insoluble complex organic chemical compounds that are essential for life. Certain insoluble proteins play a central role in biological processes and form the basis of living tissues. They consist of long chains of amino acids connected by peptide bonds and have distinct and varied three-dimensional structures, usually containing alpha helices and beta sheets as well as looping and folded chains. The present invention includes full length protein sequences of insoluble proteins, insoluble fractions of these sequences, as well as insoluble modified variants of these sequences (e.g., mutated forms, or derivatives thereof). In a particular embodiment, the protein is a full length native protein.

As used herein, the language "potential drug candidate" describes a compound that is of interest for screening against a particular protein of interest, wherein such protein is integrated into a nanodisc clathrate scaffold to form a nanodisc clathrate of the invention.

II. Nanodisc Clathrates of the Invention

It was identified that existing nanodiscs, and techniques for preparing these nanodiscs, were not effective for encapsulating fully functional, wild-type proteins that would offer true structural and activity information on native proteins. As such, the present invention provides novel molecular entities that through solution phase analysis and crystallization, allow for the examination of biologically relevant conformations of proteins in fully functional, wild-type membrane proteins without the presence of detergents.

Accordingly, the present invention provides a nanodisc clathrate comprising a protein integrated into a rigidified nanodisc clathrate scaffold. In certain embodiments, the nanodisc clathrate scaffold is comprised of a lipid combined with a lipid-free scaffold protein containing moieties suitable for cross-linking in sufficient number to achieve rigidification upon the addition of a cross-linking agent. In particular embodiments, the moieties suitable for cross-linking are lysine moieties.

In certain embodiments, the nanodisc clathrate scaffold is comprised of a lipid combined with a lipid-free scaffold protein containing moieties suitable for cross-linking in sufficient number to achieve rigidification upon the application of cross-linking chemistries. These moieties may be modified prior to cross-linking to contain chemically reactive groups suitable for controlled activation upon the addition of an activating reagent. In particular embodiments, the moieties suitable for cross-linking are lysine moieties.

In certain embodiments of the invention, the protein to be integrated within the rigidified nanodisc clathrate scaffold, forming the nanodisc clathrate is a membrane protein. Such membrane proteins may be found in biological membranes that consist of a phospholipid bilayer and a variety of proteins that accomplish vital biological functions. Membrane proteins for use herein include structural proteins, which are attached to microfilaments in the cytoskeleton which ensures stability of the cell; cell adhesion proteins, which are involved in the immune response and allow cells to identify each other and interact; membrane enzymes, which produce a variety of substances essential for cell function; membrane receptor proteins, which serve as a connection between the cell's internal and external environments; and transport proteins, e.g., carrier proteins and channel proteins, which play an important role in the maintenance of concentrations of ions. In particular embodiments, the membrane proteins of the present invention may be selected from integral membrane proteins, peripheral membrane proteins, or lipid-anchored proteins. In a specific embodiment, the membrane protein may be selected from, but not limited to, the seven transmembrane G-protein coupled receptors (GPCR's) β2AR, α2A, CB1, CCR5, GHSR, GLP1R, GCGR, GPR109A, GPR119, GPR12, GPR139, GPR182, GPR3, GPR31, GPR39, MC3R, MC4R, mGluR4, mGluR5, DRD1, and DRD3; the voltage-gated ion channels VDAC-1, Nav1.4, Cav2.1, Cav2.2, Cav2.3, and KCNK2; the multidrug transporters EmrE, TolC, MexAB-OprM, MexCD-OprJ, MexEF-OprN, MexXY, PA6N, AcrAB, MtrCDE, Ptr, and prokaryotic and eukaryotic ABC transporters (importers and exporters); the ligand gated ion channels $GABA_A$, GlyR, 5-HT, nAChR, ZAC, GluA, GluK, GluN, GluD, and P2X; the pro-apoptotic outer mitochondrial membrane protein BAK; the cell adhesion proteins IgSF CAM, addressin, integrin, cadherin, and selectin; the receptor tyrosine kinases JAK, EGFR, FGFR, VEGFR, insulin receptor, and RET; the growth factor receptors PDGFR, FGF, HGF, and NGF; immune receptors TLR, TCR, CD4, and CD28; the bacterial outer membrane proteins OprF, OprA, Porin, OmpA, OmpX, and OmpW; the channel proteins aquaporin, glyceroporin, and connexin; the membrane embedded proteases beta secretase, and gamma secretase; the lipid kinases PI3K and SphK; the cytokine receptors Type 1 interleukin receptors, Erythropoietin receptor, GM-CSF receptor, G-CSF receptor, growth hormone receptor, prolactin receptor, Oncostatin M receptor, Leukemia inhibitory factor receptor, Type II interleukin receptors, interferon-alpha/beta receptor, interferon-gamma receptor, Interleukin-1 receptor, CSF1, C-kit receptor, Interleukin-18 receptor, CD27, CD30, CD40, CD120, Lymphotoxin beta receptor, Interleukin-8 receptor, CCR1, CXCR4, MCAF receptor, NAP-2 receptor, TGF beta receptor 1, TGF beta receptor 2; light-driven transporters rhodopsin, photosystem I, and photosystem II; the transmembrane cytochrome b-like proteins cytochrome bc1, cytochrome b6f complex, formate dehydrogenase, respiratory nitrate reductase, succinate—coenzyme Q reductase (fumarate reductase), and succinate dehydrogenase; the Calcium ATPase regulators phospholamban and sarcolipin; the chloride channels CLCA, CLCN, and CLIC; the membrane-anchored proteins cytochrome c nitrite reductase complex, steryl-sulfate sulfohydrolase, stannin, glycophorin A, inovirus (filamentous phage) major coat protein, pilin, pulmonary surfactant-associated protein, monoamine oxidases A and B, fatty acid amide hydrolase, cytochrome p450 oxidases, corticosteroid 11β-dehydrogenases, and signal peptide peptidase. In one particular embodiment, the membrane protein is the glucagon peptide receptor, GCGR.

In certain embodiments, the membrane protein contains an extramembrane domain that facilitate the formation of crystal contacts.

III. Methods of the Invention

A. Methods of Preparation

The nanodisc clathrates or the nanodisc clathrate scaffolds of the present invention are not intended to be limited by the methods of preparation provided herein. However, in certain embodiments, the nanodisc clathrates may be prepared by a method comprising the steps of (a) pre-selecting a lipid-free scaffold protein to contain moieties suitable for cross-linking, and in sufficient number to achieve rigidification upon the addition of a cross-linking agent; and (b) combining the lipid-free scaffold protein, a lipid, and a protein to be integrated within a nanodisc clathrate scaffold in an environment of reduced detergent, forming a nanodisc clathrate. In certain embodiments, the method comprises the additional step of adding a cross-linking agent to the nanodisc clathrate sufficient to rigidify the nanodisc clathrate, producing a rigidified nanodisc clathrate. The nanodisc clathrates, which contain an integrated protein, and which are subjected to chemical cross-linking with a cross-linking agent, may then be purified by affinity and/or size exclusion chromatography.

In another aspect, the invention provides a method of preparation of a nanodisc clathrate comprising the steps of (a) pre-selecting a lipid-free scaffold protein to contain moieties suitable for cross-linking, and in sufficient number to achieve rigidification upon the addition of a cross-linking agent;

(b) modification of said moieties of the pre-selected, lipid-free scaffold protein to contain chemically reactive groups suitable for controlled activation upon the addition of an activating reagent; and (c) combining the modified lipid-free scaffold protein, a lipid, and a protein to be integrated within a nanodisc clathrate scaffold in an environment of reduced detergent, forming a nanodisc clathrate. In certain embodiments, the method comprises the additional steps of addition of an activating reagent and subsequent cross-linking agent to the nanodisc clathrate sufficient to rigidify the nanodisc clathrate, producing a rigidified nanodisc clathrate. The nanodisc clathrates, which contain an integrated protein, and which are subjected to chemical cross-linking with a cross-linking agent, may then be purified by affinity and/or size exclusion chromatography.

In certain embodiments, the purified nanodisc clathrates may then be evaluated for their ability to bind known ligands using fluorescence assays, radioligand binding, thermal melting analysis, surface plasmon resonance (SPR), nuclear magnetic resonance (NMR), or any combination thereof, e.g., surface plasmon resonance and thermal melting analysis. Assemblies which retain ligand binding are then put into to crystallization screening trials.

The environment of reduced detergent in which the nanodisc is formed is created by the elimination, e.g., either gradual or rapid, of detergents through the use of well-known techniques. In certain embodiments, low levels of detergent are achieved, e.g., to quantities below the critical micelle concentration (C.M.C.) of the detergent. In certain embodiments, the complete absence of detergent is achieved. In a particular embodiment, the environment of reduced detergent is achieved through the process of dialysis, with or without the use of additional removal agents, e.g., polystyrene beads (e.g., biobeads), for example as described in Example 4.

The moieties on the lipid-free scaffold protein suitable for cross-linking, e.g., also suitable for modification to contain chemically reactive groups suitable for controlled activation upon the addition of an activating reagent, may be selected from the group consisting of natural amino acids, non-natural amino acids, or peptidomimetics containing a side-chain functional group comprising a reactive group, e.g., a reactive nitrogen and suitable chain length to achieve spatial proximity to a second suitable moiety and result in chemical connectivity through the connection of a cross-linking agent. In certain embodiments, the moiety on the lipid-free scaffold protein is selected from the group consisting of lysine, cysteine, serine, threonine, glutamate, glutamine, aspartate, asparagine and tyrosine residues as well as photoreactive diazirine analogs of leucine and methionine. In a particular embodiment, the moiety suitable for cross-linking is lysine. The nanodisc clathrates of the present invention comprise at least one pair of cross-linked moieties. In certain embodiments, the nanodisc clathrates of the present invention comprise at least two pairs of cross-linked moieties, e.g., at least 5 pairs of cross-linked moieties, e.g., at least 10 pairs of cross-linked moieties, e.g., at least 15 pairs of cross-linked moieties, e.g., at least 20 pairs of cross-linked moieties.

Chemically reactive groups suitable for controlled activation upon the addition of an activating reagent may be selected based on the moieties on the lipid-free scaffold protein suitable for cross-linking, e.g., reactive nitrogens of lysine side chains. In certain embodiments, the chemically reactive group is selected from the group consisting of 3-[(2-Aminoethyl)dithio]propionic acid, citraconic anhydride, N-ϵ-maleimidocaproic acid, iodoacetic acid, methyl methanethiosulfonate, N-Succinimidyl S-acetyl(thiotetraethylene glycol), N-succinimidyl S-acetylthioacetate, N-succinimidyl-S-acetylthiopropionate, and N-ϵ-trifluoroacetylcaproyloxy]succinimide ester. In a particular embodiment, the chemically reactive group is N-succinimidyl S-acetylthioacetate.

Activating reagents suitable for use in controlled cross-linking may be selected based on the chemically reactive groups on the lipid-free scaffold protein suitable for cross-linking, e.g., chemically modified lysine side chains. In certain embodiments, the activating reagent is selected from the group consisting of 2-Mercaptoethanol, Tris(2-carboxyethyl)phosphine hydrochloride, Cysteine hydrochloride, ditiothreitol, hydroxylamine hydrochloride, and 1-Ethyl-3-[3-dimethylaminopropyl]carbodiimide hydrochloride. In certain embodiments activation can be accomplished through increases or decreases in pH. In a particular embodiment, the activating reagent is hydroxylamine hydrochloride.

Cross-linking agents useful for rigidification of the nanodisc clathrates may be selected based on the cross-linking moieties of the nanodisc clathrate, and the chemically reactive groups used to generate the modified, lipid-free scaffold protein. The cross-linking agents are reactive to specific atoms or reactive groups, e.g., reactive sulfurs, and may have different ends of the molecule that are differentially reactive to different cross-linking moieties on the nanodisc clathrate, with lengths suitable for connecting two cross-linking moieties of the nanodisc clathrate, e.g., dependent upon the length of the cross-linking moiety of the nanodisc clathrate. In certain embodiments, the cross-linking agents may be selected from the group consisting of DSG, DSS, BS3, TSAT, BS(PEG)5, BS(PEG)9, DSP, DTSSP, DST, BSOCOES, EGS, Sulfo-EGS, DMA, DMP, DMS, DTBP, DFDNB, BMOE, BMB, BMH, TMEA, BM(PEG)2, BM(PEG)3, BMDB, DTME, AMAS, BMPS, GMBS and Sulfo-GMBS, MBS and Sulfo-MBS, SMCC and Sulfo-SMCC, EMCS and Sulfo-EMCS, SMPB and Sulfo-SMPB, SMPH, LC-SMCC, Sulfo-KMUS, SM(PEG)2, SM(PEG)4, SM(PEG)6, SM(PEG)8, SM(PEG)12, SM(PEG)24, SPDP, LC-SPDP and Sulfo-LC-SPDP, SMPT, Sulfo-LC-SMPT, SIA, SBAP, SIAB, Sulfo-SIAB, DCC, EDC, PMPI, and glutaraldehyde. In a particular embodiment, the cross-linking agent is BM(PEG)3.

In another embodiment, the invention provides a method of rigidifying a nanodisc clathrate by means of cross-linking the nanodisc clathrate by the addition of a suitable cross-linking agent.

In another embodiment, the invention provides a method of preparation of a nanodisc clathrate scaffold comprising the steps of (a) pre-selecting a lipid-free scaffold protein to contain moieties suitable for cross-linking, and in sufficient number to achieve rigidification upon the addition of a cross-linking agent; and (b) combining the lipid-free scaffold protein and a lipid in an environment of reduced detergent, forming a nanodisc clathrate scaffold.

In another embodiment, the invention provides a method of preparation of a nanodisc clathrate scaffold comprising the steps of (a) pre-selecting a lipid-free scaffold protein to contain moieties suitable for cross-linking, and in sufficient number to achieve rigidification upon the addition of a cross-linking agent;

(b) modification of said moieties of the pre-selected, lipid-free scaffold protein to contain chemically reactive groups suitable for controlled activation upon the addition of an activating reagent; and (c) combining the modified lipid-free scaffold protein and a lipid in an environment of reduced detergent, forming a nanodisc clathrate scaffold.

In another embodiment, the present invention provides a method of producing X-ray quality crystals of a protein (e.g., 2.5 Angstrom resolution) comprising the step of submitting a nanodisc clathrate or the rigidified nanodisc clathrate scaffolds of the invention to crystallization screening, such that an X-ray quality crystal (e.g., 2.5 Angstrom resolution) is produced. The method may comprise subjecting the nanodisc clathrate or the rigidified nanodisc clathrate scaffolds of the invention to varying conditions of concentration, temperature and/or buffer. In certain embodiments, the crystallization screening comprises vapor-diffusion crystallization conditions. In a particular embodiment, the nanodisc clathrate may be complexed with a ligand, e.g., a small molecule (e.g., a potential drug candidate) An exemplary embodiment is described in Example 4.

B. Methods of Use

The nanodisc clathrates of the invention are particularly advantageous in structure based drug design efforts, and allow for the development of more potent, selective drugs that target proteins, e.g., membrane proteins . . . .

As such, in one embodiment, the invention provides a method of solution phase analysis of potential drug candidates comprising the steps of (a) pre-selecting a target protein for screening potential drug candidates;

(b) preparing a nanodisc clathrate comprising a protein integrated into a rigidified nanodisc clathrate scaffold, wherein the integrated protein is said target protein; and (c) combining said nanodisc clathrate with one or more potential drug candidates in solution; and (d) analyzing the results of said combination, providing a solution phase analysis of the potential drug candidates The results may be utilized to determine structure activity relationship. In certain embodiments, the results are based on in vitro analysis, e.g., a competitive binding assay to identify a pool of potential drug candidates. In certain embodiments, the nanodisc clathrate is prepared by a method comprising the steps of (a) pre-selecting a lipid-free scaffold protein to contain moieties suitable for cross-linking, and in sufficient number to achieve rigidification upon the addition of a cross-linking agent;

(b) modification of said moieties of the pre-selected, lipid-free scaffold protein to contain chemically reactive groups suitable for controlled activation upon the addition of an activating reagent; and (c) combining the modified lipid-free scaffold protein, a lipid, and a protein to be integrated within a nanodisc clathrate scaffold in an environment of reduced detergent, forming a nanodisc clathrate.

In certain embodiments, the results produced by these methods are useful for screening a series of potential drug candidates.

In additional embodiments, the present invention provides methods of antibody generation using the nanodisc clathrates of the present invention under conditions that produce antibodies, e.g., injection of nanodisc clathrates containing a membrane protein into mice, rabbits, or llamas to illicit an immune response and generate polyclonal antibodies.

In another additional embodiment, the present invention provides methods of drug delivery/formulation using the nanodisc clathrates of the present invention wherein a drug of interest to be delivered replaces the proteins described herein to be integrated into the nanodisc clathrate, and may be used as a formulation technique for the delivery of a drug to a subject.

In another embodiment, the present invention provides a kit for preparing nanodisc clathrates from insoluble proteins comprising a nanodisc clathrate scaffold and a cross-linking agent. In certain embodiments, the kit for preparing nanodisc clathrates from insoluble proteins comprises a lipid, a lipid-free scaffold protein, and a cross-linking agent, and alternatively comprising a means of producing an environment of reduced detergent. In certain embodiments, the kit also comprises instructions for use to prepare a nanodisc clathrate. In particular embodiments, the instructions for use comprise an integral component of the kit packaging.

EXEMPLIFICATION

The present invention is illustrated by the following examples, which are not intended to be limiting in any way.

Example 1

Assembly of Nanodisc Super-Discs of Membrane Proteins

Figure 2:
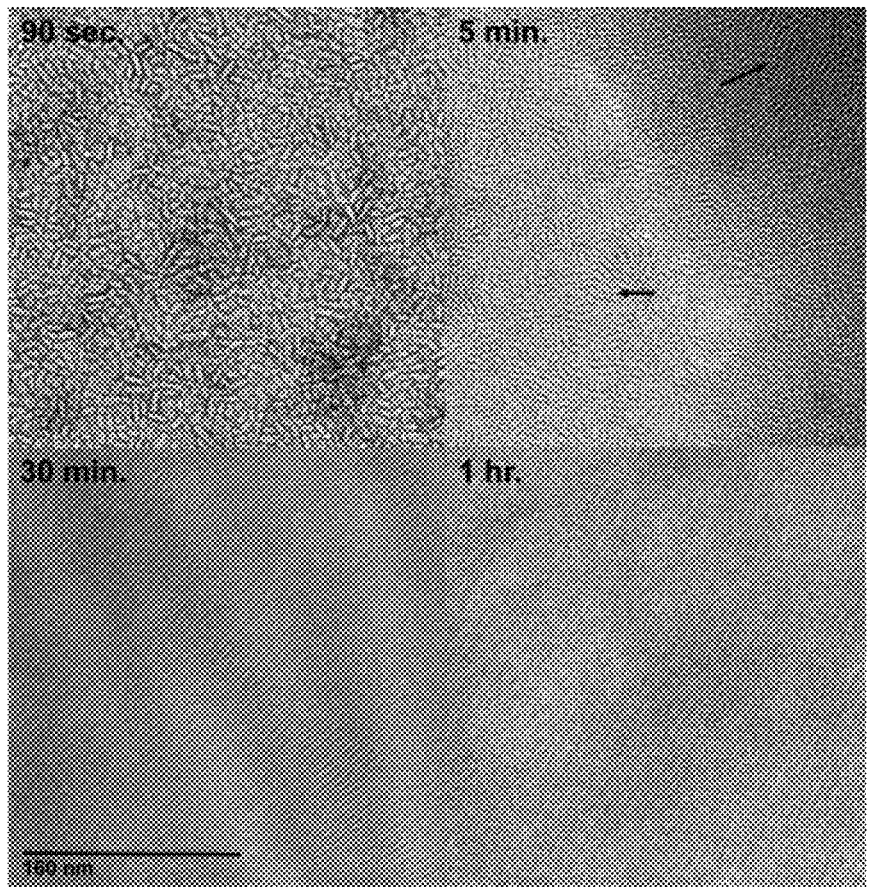
FIG. 2 depicts the TEM evaluation of nanodisc crystal formation. The process of nanodisc crystallization was monitored by Transmission Electron Microscopy (TEM). Samples were crystallized on Cu mesh grids and images taken at different time points. These images reveal the process of disc merging that begins ~5 minutes post mixing resulting in crystal formed from stacked bilayers at 1 hour post mixing.
Figure 3:
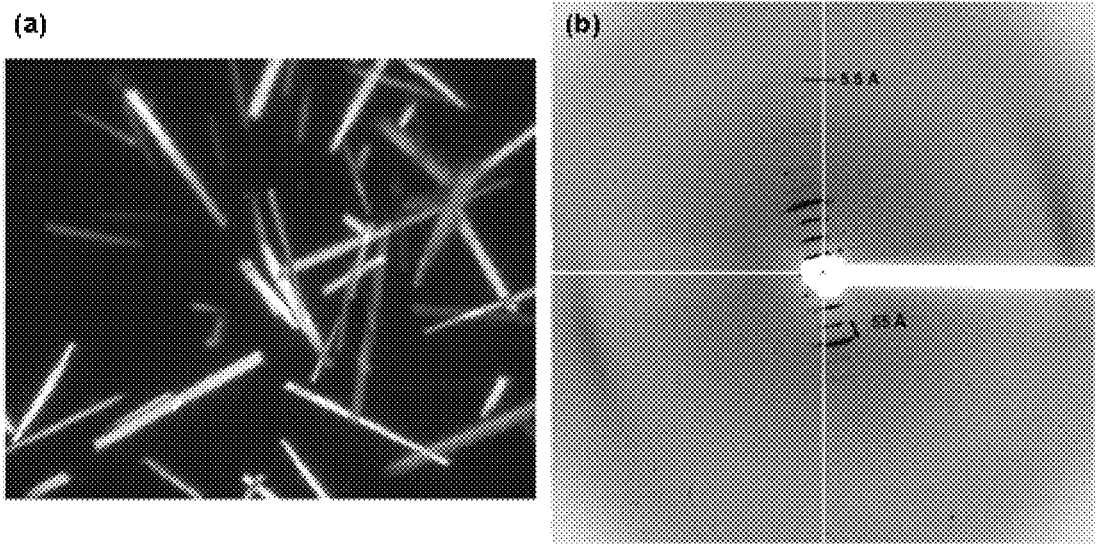
FIG. 3 depicts nanodisc crystals. (a) Crystals of lipid containing nanodiscs grown to 1 μm in length. (b) 5.5 Å diffraction pattern of lipid containing nanodiscs showing fiber diffraction characteristics. The 55 Å lattice spacing is consistent with the TEM results showing the crystal are formed from stacked bilayers.

The process of nanodisc crystallization was monitored by Transmission Electron Microscopy (TEM). Nanodiscs were prepared by mixing the detergent-solubilized, lipid-free form of the scaffold protein with lipids and removing the detergent by dialysis. The resulting assembled nanodisc clathrates were purified by size-exclusion chromatography and were crystallized on Cu mesh grids and images taken at different time points. Crystals of lipid containing nanodiscs were grown to 1 μm in length, and produced a 5.5 Å diffraction pattern of lipid containing nanodiscs showing fiber diffraction characteristics. These attempts to crystallize nanodiscs revealed that the native discs have a propensity to merge together at high concentration forming "super-discs" (FIG. 2). These super-discs can then stack on top of one another to form crystals which display fiber diffraction characteristics (FIG. 3). These images reveal the process of disc merging that begins ~5 minutes post mixing resulting in crystal formed from stacked bilayers at 1 hour post mixing. Moreover, the 55 Å lattice spacing is consistent with the TEM results showing the crystal are formed from stacked bilayers.

Example 2

Rigidified Nanodisc Clathrate Scaffold Assembly

Figure 4:
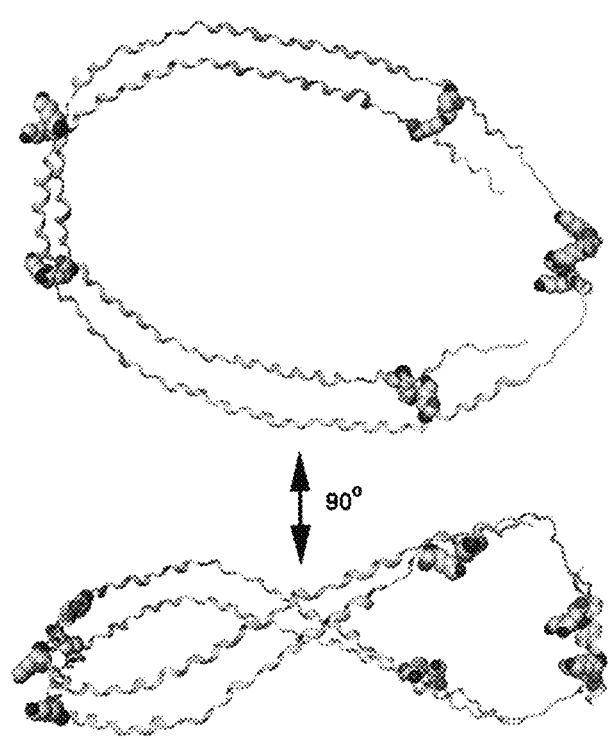
FIG. 4 depicts the crystal structure of the lipid-free form of the nanodisc scaffold protein (PDB ID 1AV1; Borhani, et al., 1997) to demonstrate spatial proximity of surface exposed lysine residues in the nanodisc scaffold protein. The crystal structure shows two copies of the protein packed together in anti-parallel fashion with their hydrophilic faces pointing out toward solvent. Analysis of the structure revealed 5 pairs of lysine residues (represented by CPK models) within close proximity that could be cross-linked to one another.

The crystal structure of the lipid-free form of the nanodisc scaffold protein (Borhani, et al., 1997, See FIG. 4 below) shows two copies (blue, peach) of the protein packed together in anti-parallel fashion with their hydrophilic faces pointing out toward solvent. Our analysis of the structure revealed 5 pairs of lysine residues within close proximity. It was our further consideration that these lysine residues were within requisite distance suitable for cross-linking to one another.

Figure 5:
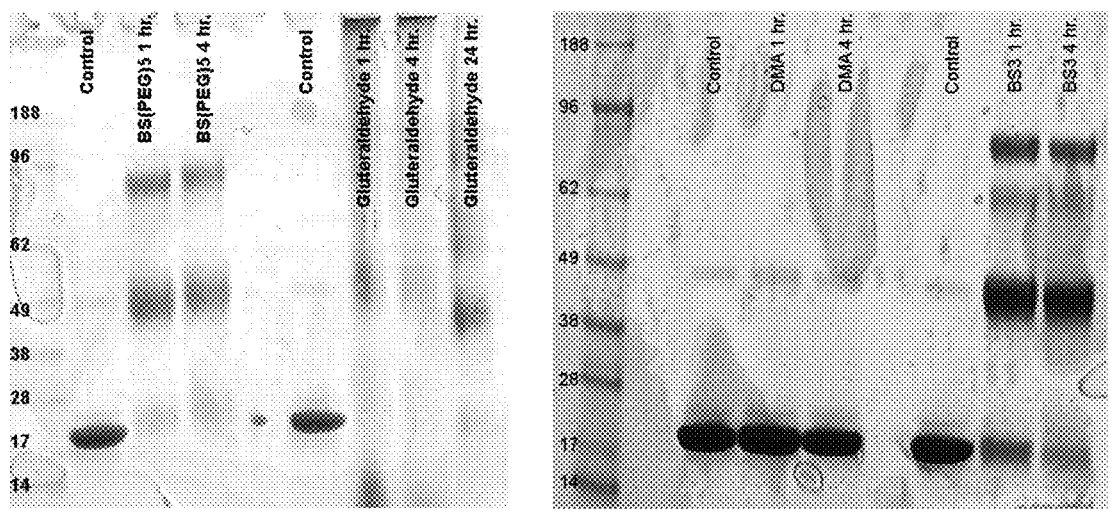
FIG. 5 depicts the SDS-PAGE analysis of the cross-linking of nanodisc clathrate scaffold. The cross-linking reagents BS(PEG)5, glutaraldehyde, DMA and BS3 were incubated with nanodisc clathrate scaffolds and reactions quenched at 1, 4 and 24 hours (glutaraldehyde). Cross-linked samples were evaluated by SDS-PAGE to determine the extent of cross-linking of the nanodisc clathrate scaffold (monomeric molecular weight 23 kDa) into dimeric nanodisc clathrate scaffolds or higher molecular weight oligomers.

Accordingly, nanodisc clathrates scaffolds of the present invention were assembled using the lipid-free membrane scaffold protein 1 (MSP1) and the lipid Palmitoyloleoyl phosphatidylcholine (POPC). Cross-linking agents which target lysine residues were added to the assembled and purified nanodisc clathrate scaffolds. In this way, multiple cross-linking reagents were evaluated for their ability to cross-link the nanodisc clathrate scaffolds and stabilize the 10 nM form of the disc. The cross-linking agents BS(PEG)5, glutaraldehyde, DMA and BS3 were incubated with the nanodisc clathrate scaffolds and reactions quenched at 1, 4 and 24 hours (glutaraldehyde). Cross-linked samples were evaluated by SDS-PAGE to determine the extent of cross-linking of the nanodisc clathrate scaffold (monomeric molecular weight 23 kDa) (FIG. 5).

Figure 6:
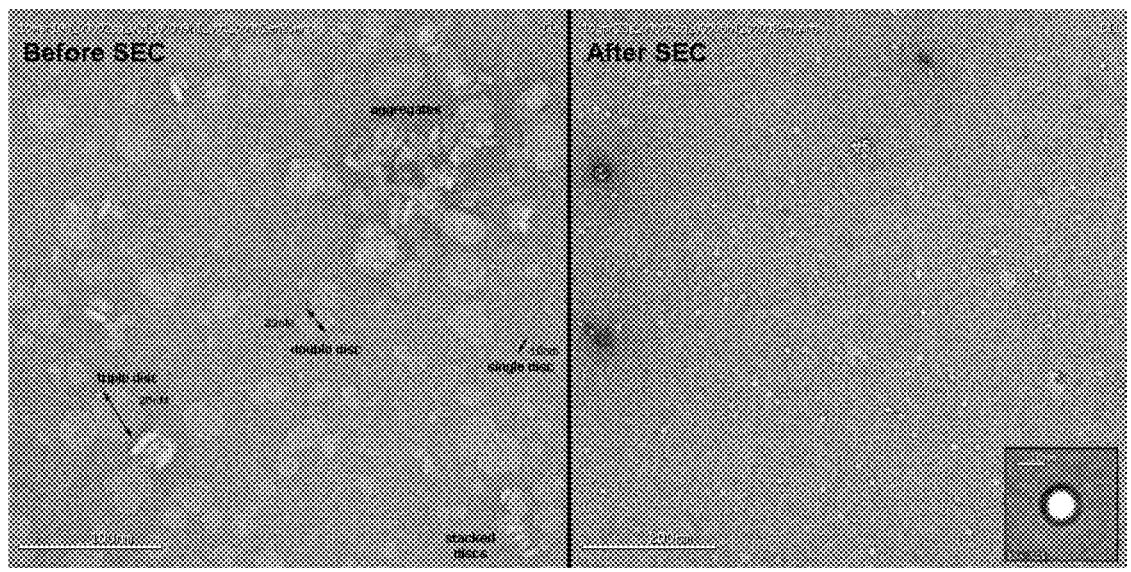
FIG. 6 depicts the TEM evaluation of BS(PEG)5 cross-linked nanodisc clathrate scaffolds. Nanodisc clathrate scaffolds were cross-linked with BS(PEG)5 and then analyzed by TEM before and after purification by size exclusion chromatography (SEC). Before SEC, the sample contains a mixture of single (10 nm), double (20 nm) and triple (30 nm) nanodisc clathrate scaffolds. After further purification with SEC, the sample is predominantly single (10 nm) nanodisc clathrate scaffolds. Class-averaged image of post-SEC nanodisc clathrate scaffolds is shown in inset.

The results of this analysis indicated that BS(PEG)5 generated the fewest number of species, a cross-linked dimer and tetramer. EM evaluation of the BS(PEG)5 cross-linked nanodisc clathrate scaffolds showed the presence of nanodisc clathrate scaffolds of 10, 20 and 30 nm diameters (FIG. 6). In order to isolate the stabilized 10 nm nanodisc clathrate scaffolds, the BS(PEG)5 cross-linked nanodisc clathrate scaffolds were further purified by size-exclusion chromatography. These purified BS(PEG)5 cross-linked nanodisc clathrate scaffolds were much more homogenous showing a sample of predominantly 10 nm discs (FIG. 6).

Before SEC, the sample contains a mixture of single (10 nm), double (20 nm) and triple (30 nm) nanodisc clathrate scaffolds. After further purification with SEC, the sample was predominantly single (10 nm) nanodisc clathrate scaffolds.

Example 3

Nanodisc Clathrate Assembly

The proteins incorporated into the nanodisc clathrate scaffolds may contain the same reactive moieties (e.g., lysine residues) as the lipid-free scaffold proteins themselves. In these embodiments, application of uncontrolled cross-linking to the protein containing nanodisc clathrates may result not only in modification of the desired moieties on the scaffold protein but also any similar reactive moieties on the incorporated proteins. The uncontrolled cross-linking of moieties on the incorporated protein would result in undesired modification of the protein and could potentially render the protein inactive or otherwise unable to adopt a biologically relevant conformation. It is, therefore, necessary, in these embodiments, to modify the lipid-free scaffold protein such that cross-linking only occurs at specific sites on the scaffold protein and does not occur on the incorporated protein.

Figure 7:
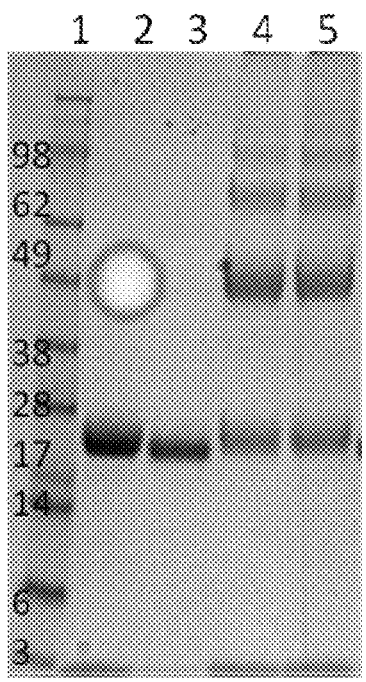
FIG. 7 depicts the SDS-PAGE analysis of generation of rigidified nanodisc clathrates. The SATA-modified lipid-free scaffold protein was mixed with the lipid POPC in a reduced detergent environment to form SATA-modified nanodisc clathrates (lane 2). These nanodisc clathrates were activated for cross-linking by the addition of hydroxylamine (lane 3). Addition of the bridging cross-linker, BM(PEG)3, results in generation of the rigidified nanodisc clathrates (lanes 4 & 5).

Previous analyses described in Example 2 had successfully identified that the cross-linking of lysines residues using BS(PEG)5 had provided for the generation of rigidified nanodisc clathrates with the desired dimeric form of the scaffold protein. Further experiments revealed the ability to treat the lysine residues of the lipid-free scaffold protein with N-succinimidyl S-acetylthioacetate (SATA) to generate a modified scaffold protein. The combination of the modified lipid-free scaffold protein and a lipid in an environment of reduced detergent gives rise to modified nanodisc clathrates. These modified nanodisc clathrates may then be activated for cross-linking by treatment with hydroxylamine and subsequently cross-linked by the addition of a bridging cross-linking agent, BM(PEG)3, forming the rigidified nanodisc clathrate (FIG. 7). The bridging cross-linking agent is reactive only to the modified scaffold protein and does not modify the incorporated protein which does not contain the modified lysine residues. In this way the cross-linking is site specific to the modified lysine residues of the scaffold protein.

Figure 8:
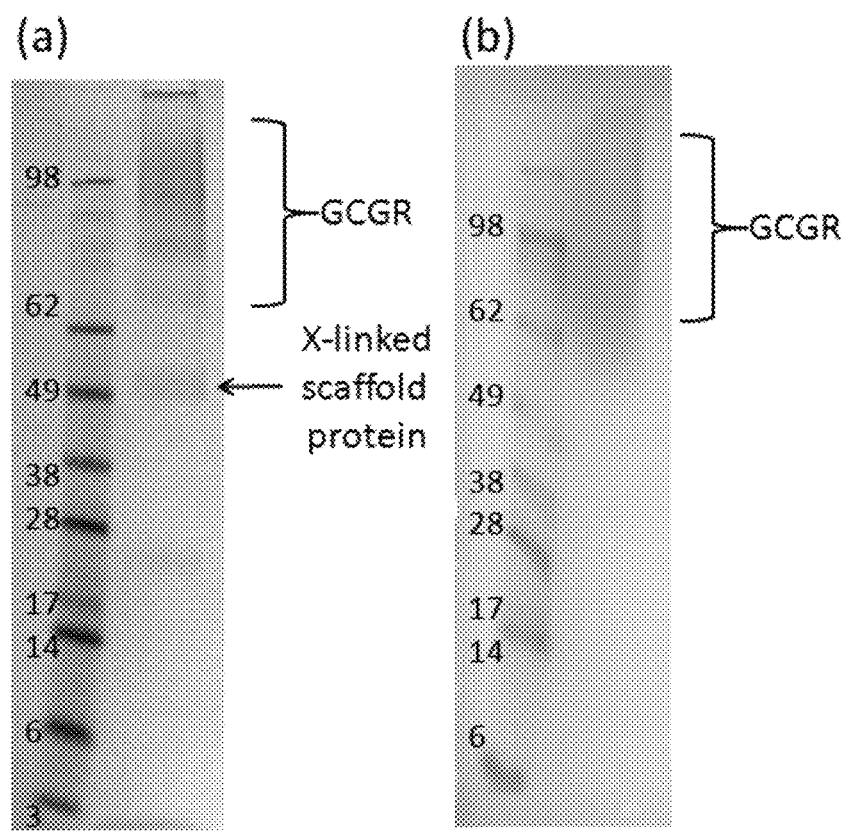
FIG. 8 depicts the SDS-PAGE and western blot analysis of GCGR incorporated into rigidified nanodisc clathrates. (a) SDS-PAGE analysis of GCGR incorporated into rigidified nanodisc clathrates generated using the controlled cross-linking of SATA-modified nanodisc scaffold protein post-assembly. The scaffold protein is now cross-linked to form a dimer of approximately 50 kDa. (b) Western blot analysis of the GCGR-containing rigidified nanodisc clathrates using an anti-FLAG antibody to confirm the presence of the receptor. The receptor contains a C-terminal FLAG tag used for affinity purification.

In this manner, the seven-transmembrane protein, glucagon receptor (GCGR) was incorporated into the modified nanodisc clathrates. The modified nanodisc clathrates underwent site-specific cross-linking with the bridging cross-linker BM(PEG)3 to generate rigidified nanodisc clathrates (FIG. 8).

Figure 9:
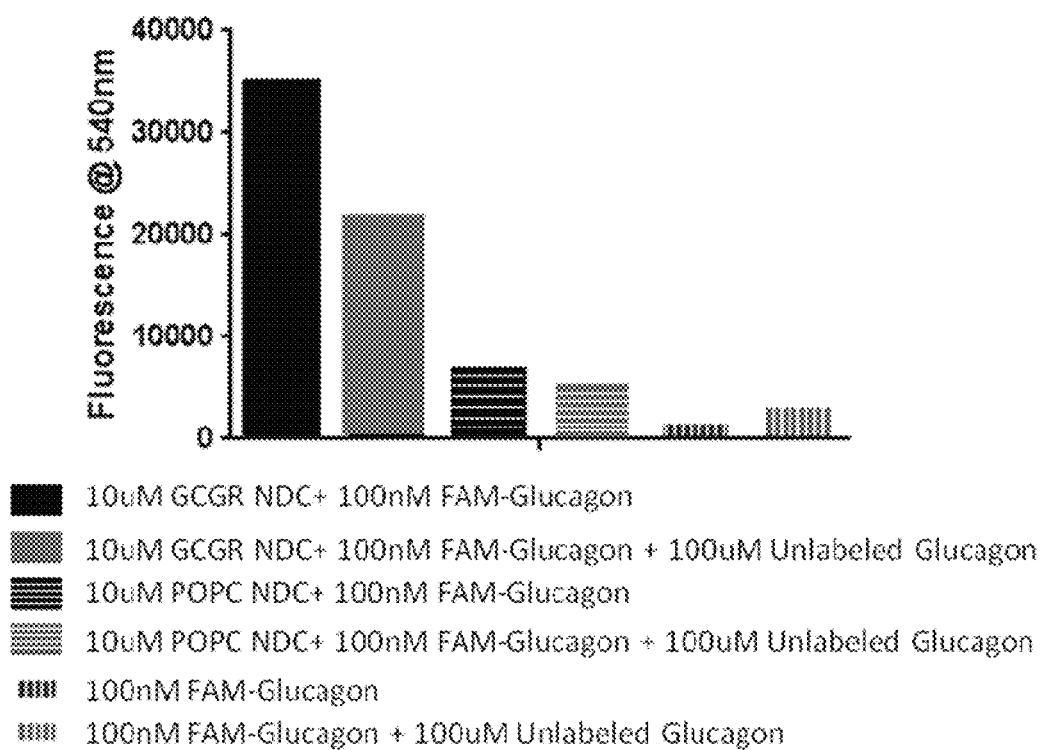
FIG. 9 depicts the fluorescent glucagon peptide binding of GCGR incorporated into rigidified nanodisc clathrates. 10 uM GCGR-containing rigidified nanodisc clathrates were mixed with 100 nM fluorescently-labeled glucagon peptide and then concentrated in an amicon centrifugal concentrator. The fluorescence in the concentrated sample was measured and compared to similarly prepared samples containing excess (100 mM) unlabeled glucagon peptide and rigidified nanodisc clathrates containing only the lipid POPC.

The GCGR receptor once incorporated into the rigidified nanodisc clathrate and subjected to the controlled activation upon the addition of an activating reagent and subsequent cross-linking, maintains its ability to bind its native ligand the glucagon peptide (FIG. 9). The GCGR-containing rigidified nanodisc clathrates were evaluated for peptide binding by the addition of fluorescently-labeled glucagon peptide and then concentrated in an amicon centrifugal concentrator. As a control, discs containing only the lipid, POPC, (POPC discs) were subjected to the same cross-linking chemistries as the GCGR-containing rigidified nanodisc clathrates and mixed with fluorescently-labeled glucagon peptide and then concentrated in an amicon centrifugal concentrator. The fluorescence retained in the concentrated material was evaluated and compared between the samples. The results shown in FIG. 9 demonstrate that the GCGR-containing rigidified nanodisc clathrates are able to bind and, therefore, retain the fluorescently labeled glucagon peptide and that this fluorescence is specific to the samples containing the incorporated receptor. We further demonstrated that the fluorescence can be reduced by the presence of excess unlabeled glucagon peptide.

Example 4

Nanodisc Clathrate Assembly

Figure 10:
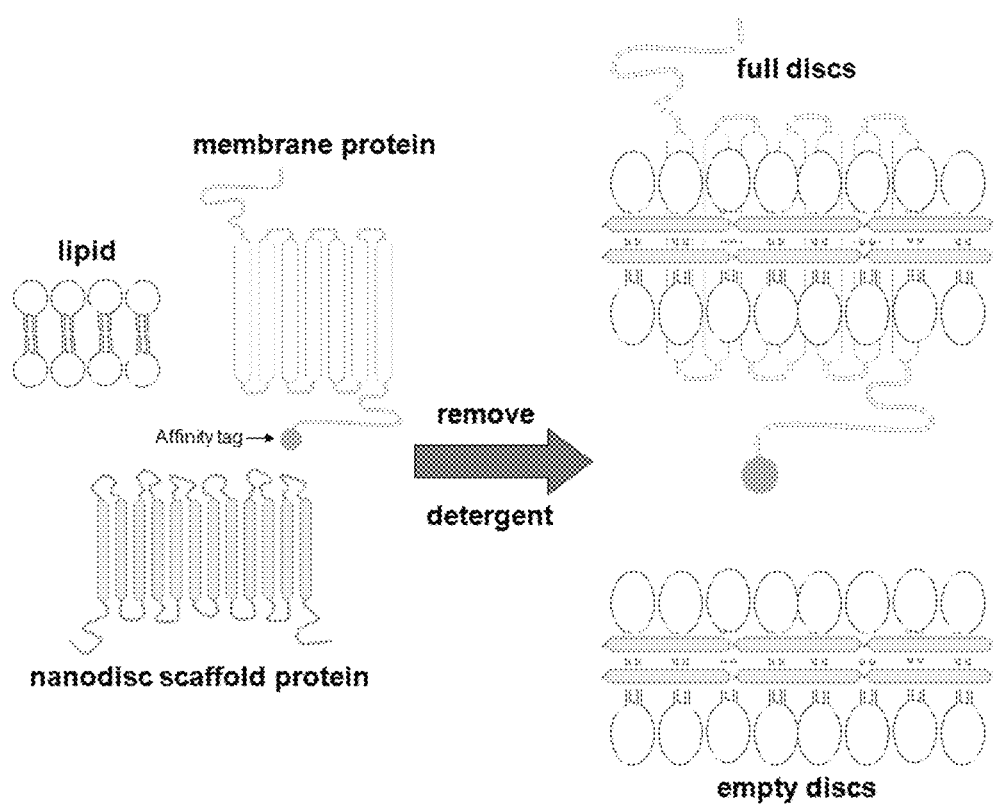
FIG. 10 illustrates the incorporation of membrane protein into a nanodisc clathrate scaffold. Membrane proteins can be incorporated into nanodisc clathrate scaffolds by mixing the protein with the nanodisc scaffold protein and lipids, and then removing the detergent. The resulting mixture will contain both empty and full nanodiscs.

Membrane proteins can be incorporated into the nanodisc clathrate scaffolds during the assembly process by including the detergent solubilized form of the protein in the assembly reaction and then removing the detergent by dialysis (Nath, et al., 2007) (FIG. 10). Polystyrene beads can also be included in the dialysis reaction to facilitate detergent removal. The nanodisc clathrate-incorporated form of the membrane protein lacks any detergent, is soluble in aqueous buffers and, therefore, is more suitable for in vitro assays, high-throughput screening or other analyses which may be negatively affected by the presence of detergents. The membrane protein inside the nanodisc is in a more native-like environment, a lipid bilayer. The lipid composition of the nanodisc can be varied to more closely mimic the native bilayer of the membrane protein.

Figure 11:
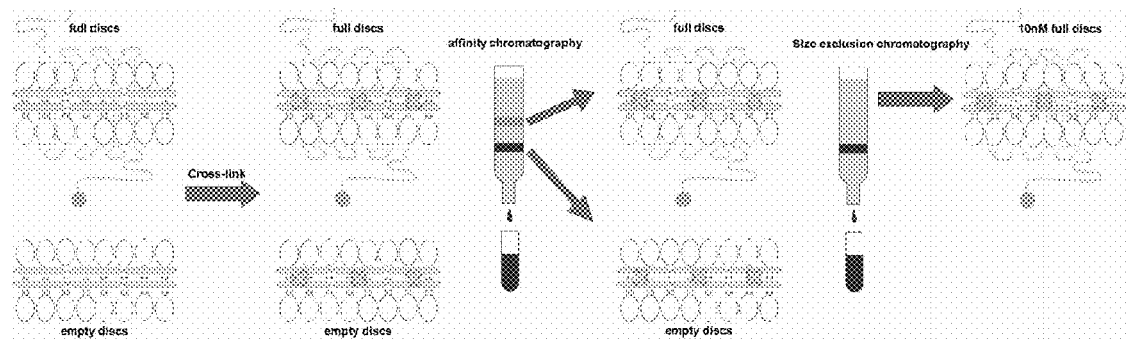
FIG. 11 illustrates the rigidification and purification of nanodisc clathrate scaffold containing a membrane protein. The nanodisc clathrate assembly containing the embedded protein is rigidified using cross linking reagents and purified by affinity and size exclusion chromatography.
Figure 12:
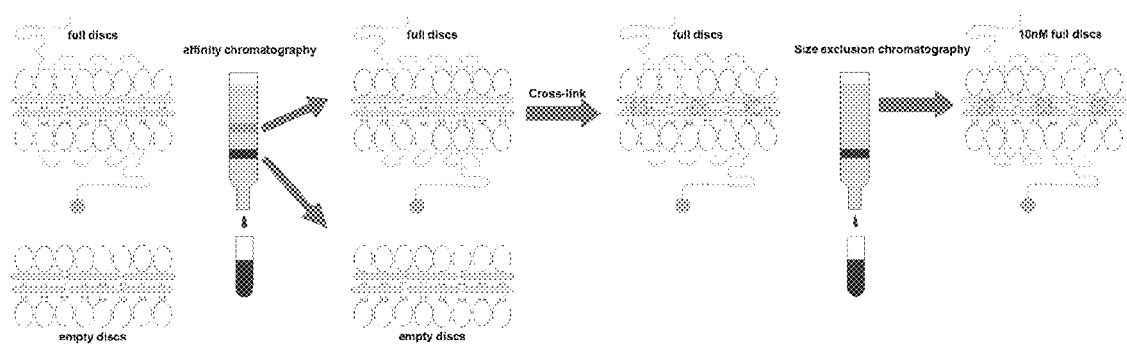
FIG. 12 illustrates the rigidification and purification of nanodisc clathrate scaffold containing a membrane protein. The nanodisc clathrate assemblies containing the embedded protein are purified by affinity chromatography, cross-linked and further purified by size exclusion chromatography to obtain the 10 nM (single) discs.

The nanodisc clathrate assembly containing the embedded protein is then rigidified using cross linking methods described herein and purified by affinity and size exclusion chromatography (FIG. 11). Alternatively the nanodisc clathrate assemblies containing the embedded protein are purified by affinity chromatography, cross-linked using the methods and reagents described herein, and further purified by size exclusion chromatography (FIG. 12).

Example 5

Crystallization of the Nanodisc Clathrate Assembly

Rigidified nanodisc clathrate scaffolds, nanodisc clathrates, and nanodisc clathrates complexed with one or more substrates or ligands may be crystallized through the use of the following:
1. Multiple concentrations of the rigidified nanodisc clathrate scaffolds, nanodisc clathrates, and nanodisc clathrates complexed with one or more substrates or ligands may be mixed with a crystallization solution at multiple ratios and volumes and equilibrated by vapor diffusion in sandwich drop, sitting drop, or hanging drop formats against a reservoir containing a crystallization solution.
2. Multiple concentrations of the rigidified nanodisc clathrate scaffolds, nanodisc clathrates, and nanodisc clathrates complexed with one or more substrates or ligands at multiple concentrations are mixed with a crystallization solution at multiple ratios and volumes and equilibrated by vapor diffusion in sandwich drop, sitting drop or hanging drop formats against a reservoir containing the crystallization solution.
3. The rigidified nanodisc clathrate scaffolds at multiple protein concentrations are mixed with a crystallization solution under oil at multiple ratios and volumes.
4. Multiple concentrations of the rigidified nanodisc clathrate scaffolds, nanodisc clathrates, and nanodisc clathrates complexed with one or more substrates or ligands. Ligands may be present at multiple protein concentrations and are mixed with a crystallization solution under oil at multiple ratios and volumes.
5. The rigidified nanodisc clathrate scaffolds at multiple protein concentrations are mixed with a crystallization solution at multiple ratios and volumes and equilibrated by dialysis against a reservoir containing a crystallization solution.
6. The rigidified nanodisc clathrate scaffolds having been complexed with substrate or ligand at multiple concentrations and present at multiple protein concentrations are mixed with a crystallization solution at multiple ratios and volumes and equilibrated by dialysis against a reservoir containing a crystallization solution.

Example 6

Use of the Nanodisc Clathrate Assemblies for Solution Phase Studies

The most common approach used for the extraction of membrane proteins from the lipid bilayer and their subsequent purification involves the use of detergents. Detergents are used to replace the native lipids which interact with the membrane associated portions of these proteins. It is thought that the detergent molecules form micelles which sequester the hydrophobic portions of the membrane proteins away from the aqueous environment but the composition and structure of these micelles is poorly understood. Many membrane proteins are unstable or inactive when extracted from the lipid bilayer into a detergent micelle. And much effort and expense is often expended in identifying suitable detergents for a given membrane protein. A more attractive approach is to place the membrane protein of interest into a native-like environment, a lipid bilayer, where it is stable and active. Nanodisc clathrate scaffolds of the present invention are an ideal solution since they provide the membrane protein with a lipid bilayer environment and, due to the presence of the scaffold protein, are soluble in aqueous solutions without detergent. The nanodisc clathrate scaffolds containing an embedded membrane protein and having been rigidified as described herein (nanodisc clathrates) may be utilized for the study of the functional properties of the embedded membrane protein using multiple solution phase techniques including, but not limited to, thermal melting analysis, surface Plasmon resonance (SPR) and nuclear magnetic resonance (NMR). These assemblies may also be utilized in high-throughput screening techniques to identify potential drug candidates.

A. Thermal Melting Analysis Technique

Using the thermal melting analysis technique, the nanodisc clathrate scaffolds containing an embedded membrane protein and having been rigidified as described herein (nanodisc clathrates) are mixed with a fluorescent dye which emits a fluorescent signal upon binding to exposed cysteine residues of the protein. This mixture is then heated over a temperature gradient at a constant rate while monitoring fluorescence. As the protein unfolds, the dye binds to the exposed cysteine residues and emits a fluorescent signal. By monitoring the fluorescence over the temperature gradient, the melting curve of the mixture is calculated. This curve is used to determine the melting temperature (Tm) of the embedded membrane protein, which is the point at which the fluorescence is increasing most rapidly. This analysis is then repeated in the presence of substrate or ligand to determine the melting temperature of the protein-substrate or protein-ligand complex. Any difference in the melting temperatures between the nanodisc clathrates and the assemblies where a substrate or ligand is present can indicate the binding of the substrate or ligand.

B. Surface Plasmon Resonance Technique

The use of the nanodisc clathrates in the surface plasmon resonance (SPR) experiments allows for the detection of substrate or ligand binding as well as the determination of the kinetic parameters of binding such as the on-rate and off-rate of the substrate or ligand. The nanodisc clathrate as described herein, is immobilized on the surface of the SPR chip and the analyte (substrate or ligand) is flowed over the surface of the chip. By measuring changes in the refractive index at the surface of the chip, the binding of the analyte is detected. The changes in refractive index over time are used to determine the kinetic's of binding of the analyte.

C. Solution Phase NMR Technique

The nanodisc clathrate as described herein is utilized in solution phase NMR techniques to observe binding of substrate or ligand and protein structure. The nanodisc clathrates containing an embedded membrane protein are placed in a buffer containing $D_2O$ and the exchange of backbone amide protons for deuterium is monitored by detecting changes in the chemical shifts of the protons. The exchange rate in the presence of substrate or ligand is also monitored. The exchange rates of the nanodisc clathrates are then compared to the exchange rates in the presence of substrate or ligand. Any differences in the exchange rates indicate substrate or ligand binding and are used to identify protein residues which interact with the substrate or ligand.

The embedded protein of the rigidified nanodisc clathrate may be labeled with $^{15}N$ and $^{13}C$ before introduction into nanodisc clathrate. This labeled protein is then used in the assembly process described herein to create the nanodisc clathrate (labeled assembly). The labeled assembly is then placed in a magnetic field and chemical shifts of the protons are monitored over a range of magnetic field frequencies. The chemical shifts at specific frequencies are used to determine the identity and connectivity of the protein atoms and, by analysis, the secondary and tertiary structure of the labeled protein.

D. High-Throughput Screening Technique

The nanodisc clathrate scaffold containing an embedded membrane protein and having been rigidified as described herein may be utilized in high-throughput screening techniques to identify potential drug candidates. These assay formats include, but are not limited to, in vitro enzyme assays, binding assays and affinity based techniques. The nanodisc clathrates are included in the assays in place of the detergent-solubilized form of the embedded membrane protein, the membrane preparation containing the embedded membrane protein or cells containing the protein of interest expressed on the cell surface. The nanodisc clathrates are mixed with substrates, detection reagents and small molecules which are potential drug candidates in multiple volumes and concentrations and activities of the small molecules libraries are determined by changes in fluorescence, fluorescence polarization, radioactivity, heat, or absorbance.

REFERENCES

1. Bayburt, T. H. & Sligar, S. G. "Self-assembly of discoidal phospholipid bilayers nanoparticles with membrane scaffold proteins" (2002) *Nanoletter.* 2: 853-856.
2. Borhani, D. W., Roger, D. P., Engler, J. A. & Brouillette, C. G. "Crystal structure of truncated human apolipoprotein A-I suggests a lipid-bound conformation" (1997) *Proc. Natl. Acad. Sci.* 94: 12291-12296.
3. Hanson, M. A., Cherezov, V., Griffith, M. T., Roth, C. B., Jaakola, V. P., Cien, E. Y., Velasquez, J., Kuhn, P. & Stevens, R.C. "A specific cholesterol binding site is established by the 2.8 angstrom structure of the human beta2-adrenergic receptor." (2008) *Structure* 16: 897-905.
4. Jaakola, V. P, Griffith, M. T., Hanson, M. A., Cherezov, V., Chein, E. Y., Lane, J. R., ljzerman, A. P. & Stevens, R. C. "The 2.6 angstrom crystal structure of human A2A adenosine receptor bound to antagonist." (2008) *Science* 322: 1211-1217.
5. Landau, E. M. & Rosenbusch, J. P. "Lipidic cubic phases: a novel concept for the crystallization of membrane proteins." (1996) *Proc. Natl. Acad. Sci.* 93: 14532-14535.
6. Nath, A., Atkins, W. & Sligar, S. G. "Applications of phospholipid bilayer nanodiscs in the study of membrane and membrane proteins." (2007) *Biochemistry.* 46: 2059-2069.
7. Nollert, P. "Lipidic cubic phases as matrices for membrane protein crystallization." (2004) *Methods* 34: 348-353.
8. Siu, F. Y., He, M., de Graaf, C., Han, G. W., Yang, D., Zhang, Z., Zhou, C., Xu, Q., Wacker, D., Joseph, J. S., Liu, W., Lau, J., Cherezov, V., Katritch, V., Wang, M. W., Stevens, R. C. "Structure of the human glucagon class B G-protein-coupled receptor." (2013) *Nature* 499: 444-449.
9. Warne, T., Serrano-Vega, M. J., Baker, J. G., Moukhametzianov, R., Edwards, P. C., Hendersen, R., Leslie, A. G., Tate, C. G. & Schertler, G. F. "Structure of beta-1-adrenergic G-protein-coupled receptor." (2008) *Nature* 454: 486-491.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. A nanodisc clathrate comprising a protein integrated into a rigidified nanodisc clathrate scaffold, wherein the rigidified nanodisc clathrate scaffold is comprised of lipid combined with a lipid-free scaffold protein selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ. ID NO: 8, SEQ ID NO: 9, SEQ ID NO: 10, SEQ ID NO: 11, SEQ ID NO: 12, SEQ ID NO: 13, and SEQ ID NO: 14.

2. The nanodisc clathrate of claim 1, wherein the rigidified nanodisc clathrate scaffold is comprised of lipid combined with a lipid-free scaffold protein containing moieties suitable for cross-linking in sufficient number to achieve rigidification upon the addition of a cross-linking agent, wherein said moieties are modified prior to cross-linking to contain chemically reactive groups suitable for controlled activation upon the addition of an activating reagent.

3. The nanodisc clathrate of claim 2, wherein the moieties suitable for cross-linking are lysine moieties.

4. The nanodisc of claim 2, wherein the chemically reactive group is selected from the group consisting of 3-[(2-Aminoethyl)dithio]propionic acid, citraconic anhydride, N-ϵ-maleimidocaproic acid, iodoacetic acid, methyl methanethiosulfonate, N-Succinimidyl S-acetyl(thiotetraethylene glycol), N-succinimidyl S-acetylthioacetate, N-succinimidyl-S-acetylthiopropionate, and N-ϵ-trifluoroacetylcaproyloxy]succinimide ester.

5. The nanodisc clathrate of claim 2, wherein the activating reagent is selected from the group consisting of 2-Mercaptoethanol, Tris(2-carboxyethyl) phosphine hydrochloride, Cysteine hydrochloride, ditiothreitol, hydroxylamine hydrochloride, and 1-Ethyl-3-[3-dimethylaminopropyl]carbodiimide hydrochloride.

6. The nanodisc clathrate of claim 2, wherein cross-linking agent is selected from the group consisting of DSG, DSS, BS3, TSAT, BS(PEG)5, BS(PEG)9, DSP, DTSSP, DST, BSOCOES, EGS, Sulfo-EGS, DMA, DMP, DMS, DTBP, DFDNB, BMOE, BMB, BMH, TMEA, BM(PEG)2, BM(PEG)3, BMDB, DTME, AMAS, BMPS, GMBS and Sulfo-GMBS, MBS and Sulfo-MBS, SMCC and Sulfo-SMCC, EMCS and Sulfo-EMCS, SMPB and Sulfo-SMPB, SMPH, LC-SMCC, Sulfo-KMUS, SM(PEG)2, SM(PEG)4, SM(PEG)6, SM(PEG)8, SM(PEG)12, SM(PEG)24, SPDP, LC-SPDP and Sulfo-LC-SPDP, SMPT, Sulfo-LC-SMPT, SIA, SBAP, SIAB, Sulfo-SIAB, DCC, EDC, PMPI, and glutaraldehyde.

7. The nanodisc clathrate of claim 1, wherein the protein is a membrane protein.

8. The nanodisc clathrate of claim 7, wherein the membrane protein is selected from the group consisting of the transmembrane G-protein coupled receptors β2AR, α2A, CB1, CCR5, GHSR, GLP1R, GCGR, GPR109A, GPR119, GPR12, GPR139, GPR182, GPR3, GPR31, GPR39, MC3R, MC4R, mGluR4, mGluR5, DRD1, and DRD3; the voltage-gated ion channels VDAC-1, Nav1.4, Cav2.1, Cav2.2, Cav2.3, and KCNK2; the multidrug transporters EmrE, TolC, MexAB-OprM, MexCD-OprJ, MexEF-OprN, MexXY, PAβN, AcrAB, MtrCDE, Ptr, and prokaryotic and eukaryotic ABC transporters (importers and exporters); the ligand gated ion channels $GABA_A$, GlyR, 5-HT, nAChR, ZAC, GluA, GluK, GluN, GluD, and P2X; the pro-apoptotic outer mitochondrial membrane protein BAK; the cell adhesion proteins IgSF CAM, addressin, integrin, cadherin, and selectin; the receptor tyrosine kinases JAK, EGFR, FGFR, VEGFR, insulin receptor, and RET; the growth factor receptors PDGFR, FGF, HGF, and NGF; immune receptors TLR, TCR, CD4, and CD28; the bacterial outer membrane proteins OprF, OprA, Porin, OmpA, OmpX, and OmpW; the channel proteins aquaporin, glyceroporin, and connexin; the membrane embedded proteases beta secretase, and gamma secretase; the lipid kinases PI3K and SphK; the cytokine receptors Type 1 interleukin receptors, Erythropoietin receptor, GM-CSF receptor, G-CSF receptor, growth hormone receptor, prolactin receptor, Oncostatin M receptor, Leukemia inhibitory factor receptor, Type II interleukin receptors, interferon-alpha/beta receptor, interferon-gamma receptor, Interleukin-1 receptor, CSF1, C-kit receptor, Interleukin-18 receptor, CD27, CD30, CD40, CD120, Lymphotoxin beta receptor, Interleukin-8 receptor, CCR1, CXCR4, MCAF receptor, NAP-2 receptor, TGF beta receptor 1, TGF beta receptor 2; light-driven transporters rhodopsin, photosystem I, and photosystem II; the transmembrane cytochrome b-like proteins cytochrome bc1, cytochrome b6f complex, formate dehydrogenase, respiratory nitrate reductase, succinate-coenzyme Q reductase (fumarate reductase), and succinate dehydrogenase; the Calcium ATPase regulators phospholamban and sarcolipin; the chloride channels CLCA, CLCN, and CLIC; and the membrane-anchored proteins cytochrome c nitrite reductase complex, steryl-sulfate sulfohydrolase, stannin, glycophorin A, inovirus (filamentous phage) major coat protein, pilin, pulmonary surfactant-associated protein, monoamine oxidases A and B, fatty acid amide hydrolase, cytochrome p450 oxidases, corticosteroid 11β-dehydrogenases, and signal peptide peptidase.

9. The nanodisc clathrate of claim 8, wherein the membrane protein contains an extramembrane domain that facilitates the formation of crystal contacts for producing X-ray quality crystals of the membrane protein.

10. The nanodisc clathrate of claim 8, wherein the membrane protein is glucagon peptide receptor, GCGR.

11. A method of preparation of the rigidified nanodisc clathrate scaffold in claim 1 comprising the steps of
   (a) pre-selecting a lipid-free scaffold protein to contain moieties suitable for cross linking, and in sufficient number to achieve rigidification upon the addition of a cross-linking agent;
   (b) modifying said moieties of the pre-selected, lipid-free scaffold protein to contain chemically reactive groups suitable for controlled activation upon the addition of an activating reagent; and
   (c) combining the modified lipid-free scaffold protein and a lipid in an environment of reduced detergent, forming the rigidified nanodisc clathrate scaffold in claim 1.

12. The method of claim 11 comprising the additional step of adding an activating reagent to produce controlled activation of the chemical reactive groups.

13. A method of preparation of the nanodisc clathrate of claim 1 comprising the steps of
   (a) pre-selecting a lipid-free scaffold protein to contain moieties suitable for cross linking, and in sufficient number to achieve rigidification upon the addition of a cross-linking agent;
   (b) modifying said moieties of the pre-selected lipid-free scaffold protein to contain chemically reactive groups suitable for controlled activation upon the addition of an activating reagent; and
   (c) combining the modified lipid-free scaffold protein, a lipid, and a protein to be integrated within a nanodisc clathrate scaffold in an environment of reduced detergent, forming the nanodisc clathrate of claim 1.

14. The method of claim 13 comprising the additional step of adding an activating reagent to produce controlled activation of the chemical reactive groups.

15. The method of claim 13 comprising the additional step of adding a cross-linking agent to the nanodisc clathrate sufficient to rigidify the nanodisc clathrate, producing a rigidified nanodisc clathrate.

16. A method of producing X-ray quality crystals of a protein comprising the step of submitting the nanodisc clathrate of claim 1 to crystallization screening, such that an X-ray quality crystal is produced.

17. The method of claim 16 wherein the crystallization screening comprises vapor-diffusion crystallization conditions.

18. A method of solution phase analysis of potential drug candidates comprising the steps of
   (a) pre-selecting a target protein for screening potential drug candidates;
   (b) preparing the nanodisc clathrate of claim 1 comprising a protein integrated into a rigidified nanodisc clathrate scaffold, wherein the integrated protein is said target protein;
   (c) combining said nanodisc clathrate from step (b) with one or more potential drug candidates in solution; and
   (d) analyzing the results of said combination, providing a solution phase analysis of the potential drug candidates.

19. The method of claim 18, wherein the results are used to determine a structure activity relationship.

20. The method of claim 18, wherein the results are based on in vitro analysis.

21. The method of claim 20, wherein the analysis is based on a competitive binding assay.

22. The method of claim 18, wherein the results are useful for screening a series of potential drug candidates.

\* \* \* \* \*